United States Patent
Hama et al.

(10) Patent No.: US 11,738,338 B2
(45) Date of Patent: Aug. 29, 2023

(54) TEST CONTAINER FOR EXAMINATION

(71) Applicant: FUJIFILM Corporation, Tokyo (JP)

(72) Inventors: Takeshi Hama, Ashigarakami-gun (JP); Noboru Komori, Ashigarakami-gun (JP); Yuki Inoue, Ashigarakami-gun (JP); Aya Ouchi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 216 days.

(21) Appl. No.: 16/950,434

(22) Filed: Nov. 17, 2020

(65) Prior Publication Data

US 2021/0170404 A1 Jun. 10, 2021

(30) Foreign Application Priority Data

Dec. 9, 2019 (JP) .................................. 2019-222329

(51) Int. Cl.
*B01L 3/00* (2006.01)
*G01N 33/543* (2006.01)

(52) U.S. Cl.
CPC .. *B01L 3/502715* (2013.01); *G01N 33/54366* (2013.01); *B01L 2300/123* (2013.01); *B01L 2400/0406* (2013.01)

(58) Field of Classification Search
CPC ............. B01L 3/502715; B01L 3/5023; B01L 2300/123; B01L 2300/0816; B01L 2300/0877; B01L 2300/0887; B01L 2400/0406; B01L 2400/0478; B01L 2400/0481; B01L 2200/16; G01N 33/54366
See application file for complete search history.

(56) References Cited

U.S. PATENT DOCUMENTS 7,497,997 B2 * 3/2009 Glezer .................... B01L 9/527
435/7.1
2007/0082331 A1 4/2007 Tanaami et al.
(Continued)

FOREIGN PATENT DOCUMENTS

JP 2003-139662 A 5/2003
JP 2003-166910 A 6/2003
(Continued)

OTHER PUBLICATIONS

Japanese Office Action for corresponding Japanese Application No. 2019-222329, dated Nov. 15, 2022, with English translation.

*Primary Examiner* — Jennifer Wecker
*Assistant Examiner* — Alea N. Martin
(74) *Attorney, Agent, or Firm* — Birch, Stewart, Kolasch & Birch, LLP

(57) ABSTRACT

A test container including: at least two accommodation portions each accommodating a liquid and internally provided; a flow path connecting the two accommodation portions to each other at respective upper end positions thereof internally provided; and a flexible film deformable inwards of at least one accommodation portion at a portion forming an upper wall surface of the one accommodation portion, in which the liquid accommodated in the one accommodation portion is fed to the other accommodation portion via the flow path due to deformation of the flexible film towards the one accommodation portion, and a breaking elongation of the flexible film is 100% or more and 600% or less.

16 Claims, 13 Drawing Sheets

(56) References Cited

U.S. PATENT DOCUMENTS

| | | | |
|---|---|---|---|
| 2008/0217246 A1* | 9/2008 | Benn | G01N 35/00029 |
| | | | 422/63 |
| 2011/0053289 A1* | 3/2011 | Lowe | B01L 3/502769 |
| | | | 436/501 |
| 2011/0120580 A1 | 5/2011 | Takahashi | |
| 2018/0290230 A1* | 10/2018 | Kawashima | B29C 65/08 |
| 2020/0088739 A1* | 3/2020 | Rogers | B01L 3/502707 |

FOREIGN PATENT DOCUMENTS

| | | |
|---|---|---|
| JP | 2007-101428 A | 4/2007 |
| JP | 2010-75072 A | 4/2010 |
| JP | 2010-99061 A | 5/2010 |
| JP | 2010-107211 A | 5/2010 |
| JP | 2011-232223 A | 11/2011 |

* cited by examiner

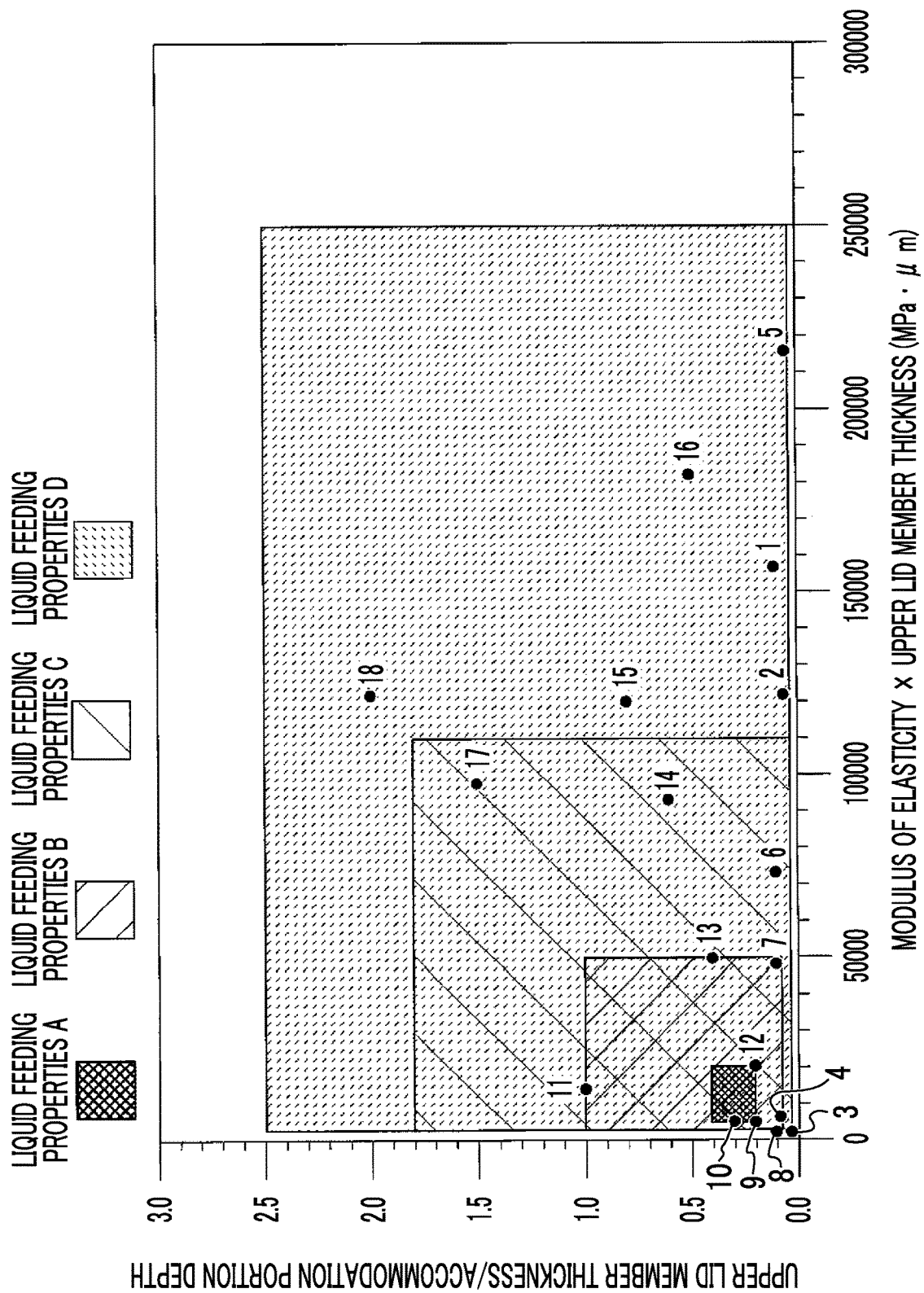

TEST CONTAINER FOR EXAMINATION

CROSS-REFERENCE TO RELATED APPLICATIONS

The present application claims priority under 35 U.S.C. § 119 to Japanese Patent Application No. 2019-222329 filed on Dec. 9, 2019. The above application is hereby expressly incorporated by reference, in its entirety, into the present application.

BACKGROUND OF THE INVENTION

1. Field of the Invention

The technology of the present disclosure relates to a test container.

2. Description of the Related Art

Test containers such as a test cartridge, an analysis chip, and the like used for performing various analyses with respect to a specimen extracted from a biological sample are known.

JP2007-101428A discloses a cartridge for a chemical treatment having a plurality of wells (liquid accommodation portions) accommodating a liquid and configured by stacking an elastic member having a plurality of recesses on one surface on a substrate so that the recesses face the substrate side, and a flow path connecting between the wells. JP2007-101428A discloses a method for rotating a roller while pressing the elastic member of a cartridge for elastic deformation of the elastic member, to cause pressing of a liquid in the elastically deformed well to move to an adjacent well via the flow path connected to the well.

JP2003-166910A discloses a liquid feeding mechanism which feeds a liquid filled in a liquid tank to a flow path connected to the liquid tank by changing a volume of the liquid tank (liquid accommodation portion) formed to surround a wall, and an analysis device having the liquid feeding mechanism.

SUMMARY OF THE INVENTION

However, in JP2007-101428A and JP2003-166910A, a liquid is fed by deforming an elastic member, but there is no specific description about physical properties suitable as the elastic member. In addition, in the test container disclosed in both JP2007-101428A and JP2003-166910A, the flow path connecting the liquid accommodation portions is disposed to connect lower ends of the liquid accommodation portions, and accordingly, even in a case where an external force is not applied, the liquid may pass the flow path and flow into the adjacent accommodation portion due to a capillary force or the like.

Therefore, it is necessary to provide a test container which does not allow a flow of a liquid from an accommodation portion that holds the liquid to an adjacent accommodation portion, in a case where no external force is applied, and which has excellent liquid feeding properties, in a case of feeding the liquid by applying the external force.

The technology of the present disclosure is made in view of the above circumstance, and an object thereof is to provide a test container, comprising at least two accommodation portions capable of accommodating a liquid and having excellent liquid feeding properties.

There is provided a test container of the present disclosure comprising: at least two accommodation portions each capable of accommodating a liquid and internally provided; a flow path connecting the two accommodation portions to each other at respective upper end positions thereof and internally provided; and a flexible film deformable inwards of at least one accommodation portion at a portion forming an upper wall surface of the one accommodation portion, in which the liquid accommodated in the one accommodation portion is fed to the other accommodation portion via the flow path due to deformation of the flexible film towards the one accommodation portion, and a breaking elongation of the flexible film is 100% to 600%.

In the test container of the present disclosure,
it is preferable that, in a case where a thickness of the flexible film is t μm, a modulus of elasticity of the flexible film is α MPa, and a depth of the one accommodation portion is d μm,
relationships of $0.03 \le t/d \le 2.5$ and $2{,}000 \le \alpha \times t \le 250{,}000$ are satisfied.

In the test container of the present disclosure,
it is preferable that relationships of $0.03 \le t/d \le 1.8$ and $2{,}000 \le \alpha \times t \le 110{,}000$ are satisfied.

In the test container of the present disclosure,
it is preferable that relationships of $0.08 \le t/d \le 1.0$ and $2{,}000 \le \alpha \times t \le 50{,}000$ are satisfied.

In the test container of the present disclosure,
it is preferable that relationships of $0.2 \le t/d \le 0.4$ and $4{,}000 \le \alpha \times t \le 20{,}000$ are satisfied.

In the test container of the present disclosure, it is preferable that the breaking elongation is 200% to 500%.

It is preferable that the test container of the present disclosure further comprises: a container main body portion in which a portion forming each of the at least two accommodation portions and the flow path is open; and an upper lid member including the flexible film, and the at least two accommodation portions and the flow path are formed by covering the opening of the container main body portion with the upper lid member.

In the test container of the present disclosure, the upper lid member may have flexibility over an entire area.

In the test container of the present disclosure, it is preferable that the flexible film consist of any of a silicone resin, a fluororesin, polyolefin, and polycarbonate.

The test container of the present disclosure may further comprise a first accommodation portion; a second accommodation portion as the one accommodation portion; a third accommodation portion as the other accommodation portion; a first flow path connecting the first accommodation portion and the second accommodation portion to each other at respective upper end positions thereof; and a second flow path connecting the second accommodation portion and the third accommodation portion to each other at respective upper end positions thereof.

The test container of the present disclosure may further comprise a liquid return prevention structure which prevents a backflow of the liquid to the first accommodation portion, in a case where the liquid accommodated in the second accommodation portion is fed to the third accommodation portion via the second flow path due to deformation of the flexible film toward the second accommodation portion.

In the test container of the present disclosure, the liquid return prevention structure may have a structure in which a height from an inner bottom surface of the second accommodation portion to an inner bottom surface of the first flow path is higher than a height from the inner bottom surface of the second accommodation portion to an inner bottom surface of the second flow path.

In the test container of the present disclosure, the liquid return prevention structure may have a structure of the first flow path and the second flow path in which a water contact angle of an inner surface of the first flow path is set to be greater than a water contact angle of an inner surface of the second flow path.

In the test container of the present disclosure, the liquid return prevention structure may have a structure of a stepped portion which is provided between the first flow path and the second accommodation portion and which includes two or more steps from an inner bottom surface of the second accommodation portion.

The test container of the present disclosure may further include a chromatographic carrier for performing a nucleic acid test, and a carrier accommodation portion accommodating the chromatographic carrier.

In the test container of the present disclosure, the first accommodation portion may accommodate a first liquid containing magnetic particles, the second accommodation portion may accommodate separated magnetic particles separated from the first liquid, and the first flow path may allow the separated magnetic particles to pass.

According to the technology of the present disclosure, it is possible to obtain excellent liquid feeding properties in a test container comprising at least two accommodation portions each capable of accommodating a liquid.

BRIEF DESCRIPTION OF THE DRAWINGS

FIG. 17 is a diagram showing a relationship between upper lid member thickness/accommodation portion depth, modulus of elasticity×upper lid member thickness, and liquid feeding properties.

DESCRIPTION OF THE PREFERRED EMBODIMENTS

Figure 1:
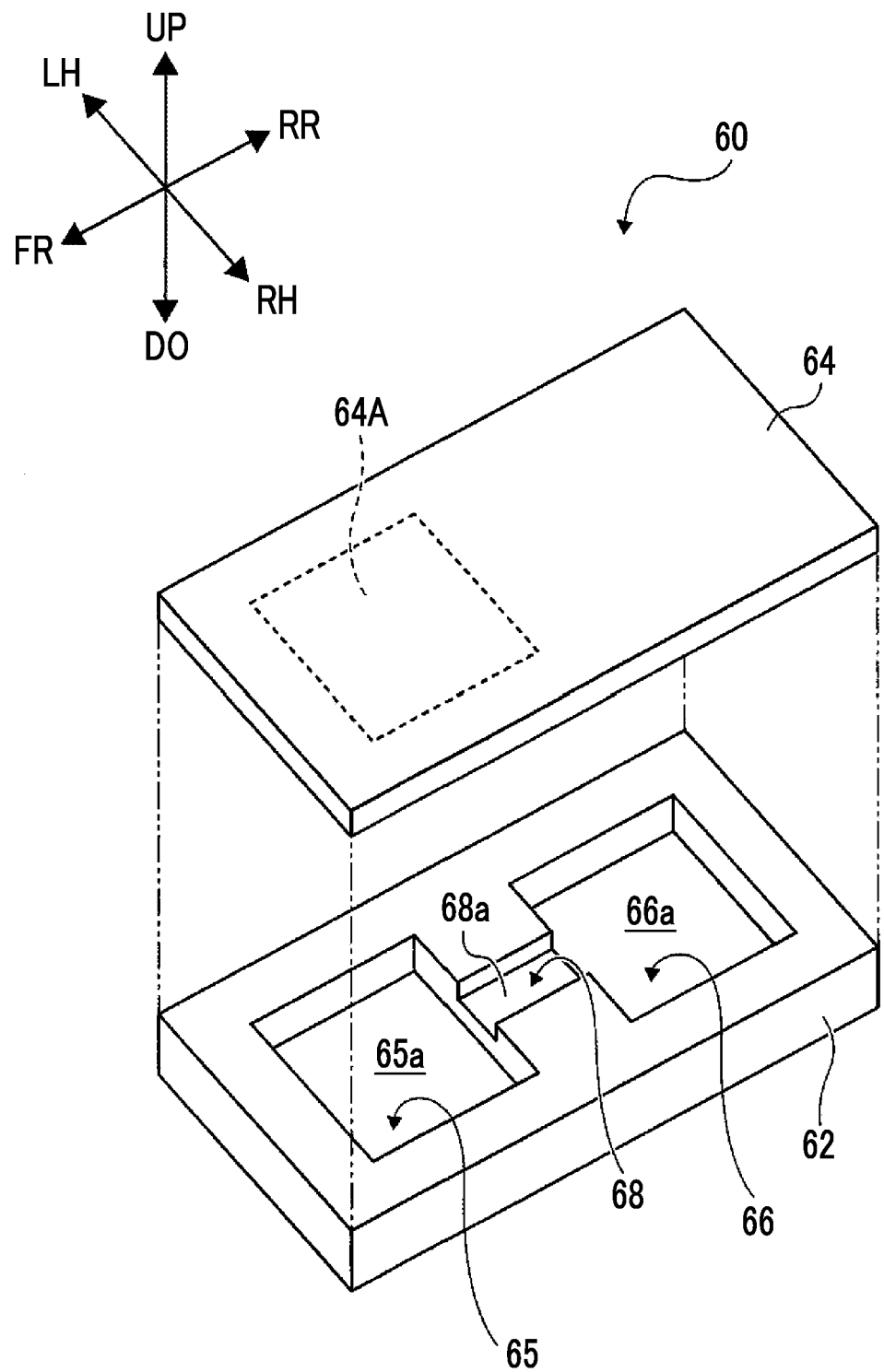
FIG. 1 is a perspective view showing a schematic configuration of a test container 60.

Hereinafter, an example of an embodiment according to the present invention will be described with reference to the drawings. A front direction, a rear direction, an upward direction, a downward direction, a left direction, and a right direction used in the description below correspond to "FR", "RR", "UP", "DO", "LH", and "RH", respectively, in the each drawing. Since these directions are defined for convenience of description, a device configuration is not limited to these directions. The FR side is an upstream side and the RR side is a downstream side in the use of a container. In addition, the scales and the like of the respective constituent elements in the drawings are suitably changed from the actual scales for the sake of easy visual recognition.

Test Container of One Embodiment

Figure 2:
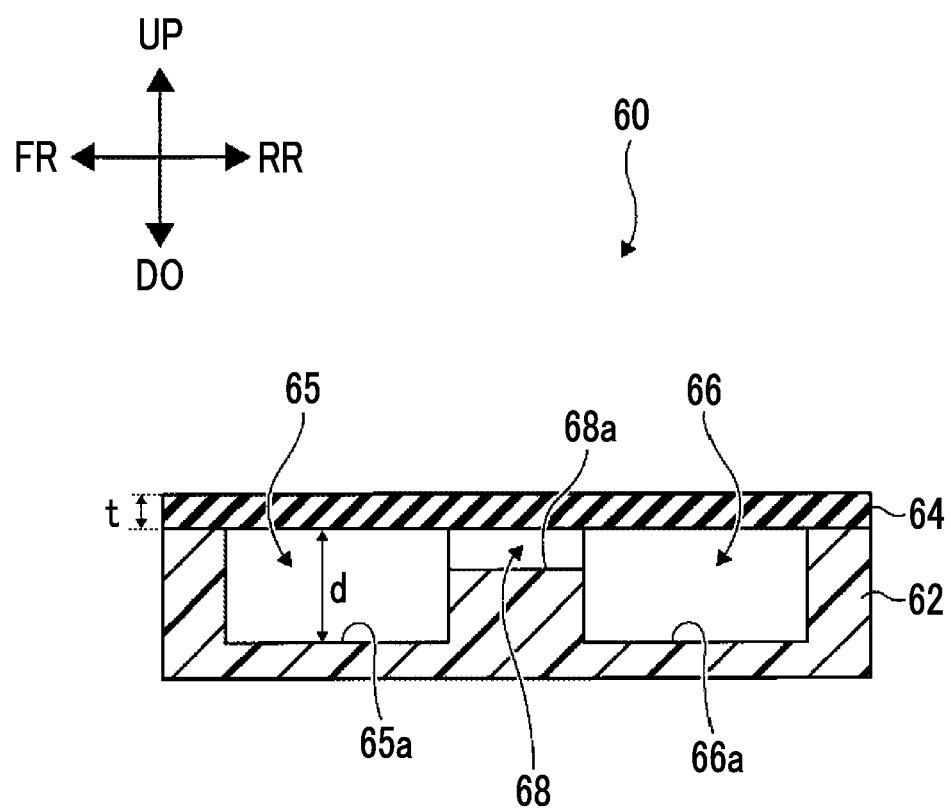
FIG. 2 is a cross-sectional view showing a schematic configuration of the test container 60.

A test container 60 according to one embodiment will be described. FIG. 1 is an exploded perspective view showing a schematic configuration of the test container 1. FIG. 2 is a cross-sectional view showing a schematic configuration of the test container 60.

The test container 60 is internally provided with at least two accommodation portions 65 and 66 each capable of accommodating a liquid and a flow path 68 connecting the two accommodation portions 65 and 66 to each other at respective upper end positions thereof, and a portion 64A forming an upper wall surface 65b of the at least one accommodation portion 65 consists of a flexible film that is deformable inwards of the accommodation portion 65. The test container 60 feeds the liquid accommodated in the one accommodation portion 65 to the other accommodation portion 66 via the flow path 68 by deforming the flexible film toward the one accommodation portion 65.

Here, a breaking elongation of the flexible film is 100% to 600%.

In this example, the test container 60 includes a main body portion 62 and an upper lid member 64. The main body portion 62 has an opening at a portion forming each of the two accommodation portions 65 and 66 and the flow path 68. The test container has a configuration in which the two accommodation portions 65 and 66 and the flow path 68 are formed therein by covering the opening of the main body portion 62 with the upper lid member 64. That is, the main body portion 62 configures inner bottom surfaces 65a and 66a and side wall surfaces of the accommodation portions 65 and 66, and an inner bottom surface 68a and a side wall surface of the flow path 68, and the upper lid member 64 configures upper wall surfaces 65b and 66b of the accommodation portions 65 and 66 and an upper wall surface 68b of the flow path 68. However, the present invention is not limited to this configuration, as long as it has a configuration of including each accommodation portion and each flow path therein.

In this example, the upper lid member 64 has flexibility throughout. However, the entire upper lid member 64 may not have to be flexible, as long as the portion 64A configuring at least the upper wall surface 65b of the at least one accommodation portion 65 of the test container 60, that is, the portion 64A of the upper lid member 64 has a flexible portion deformable in a direction toward the accommodation portion 65.

The test container 60 includes the flow path 68 at the upper end position of the two accommodation portions 65 and 66. Accordingly, the liquid accommodated in the accommodation portion is difficult to flow into the flow path, compared to a case where the flow path is included at a lower end or in the middle. Therefore, it is possible to prevent a passage of the liquid into the flow path due to a capillary phenomenon or the like without applying an external force. Meanwhile, since the portion 64A deformable toward the inside of the accommodation portion 65 is included at the upper portion of the one accommodation portion 65, the portion 64A is deformed toward the inside of the accommodation portion 65 to reduce a volume of the accommodation portion 65, thereby simply realizing liquid feeding to the other accommodation portion 66 by pushing the liquid accommodated in the accommodation portion 65.

Figure 3:
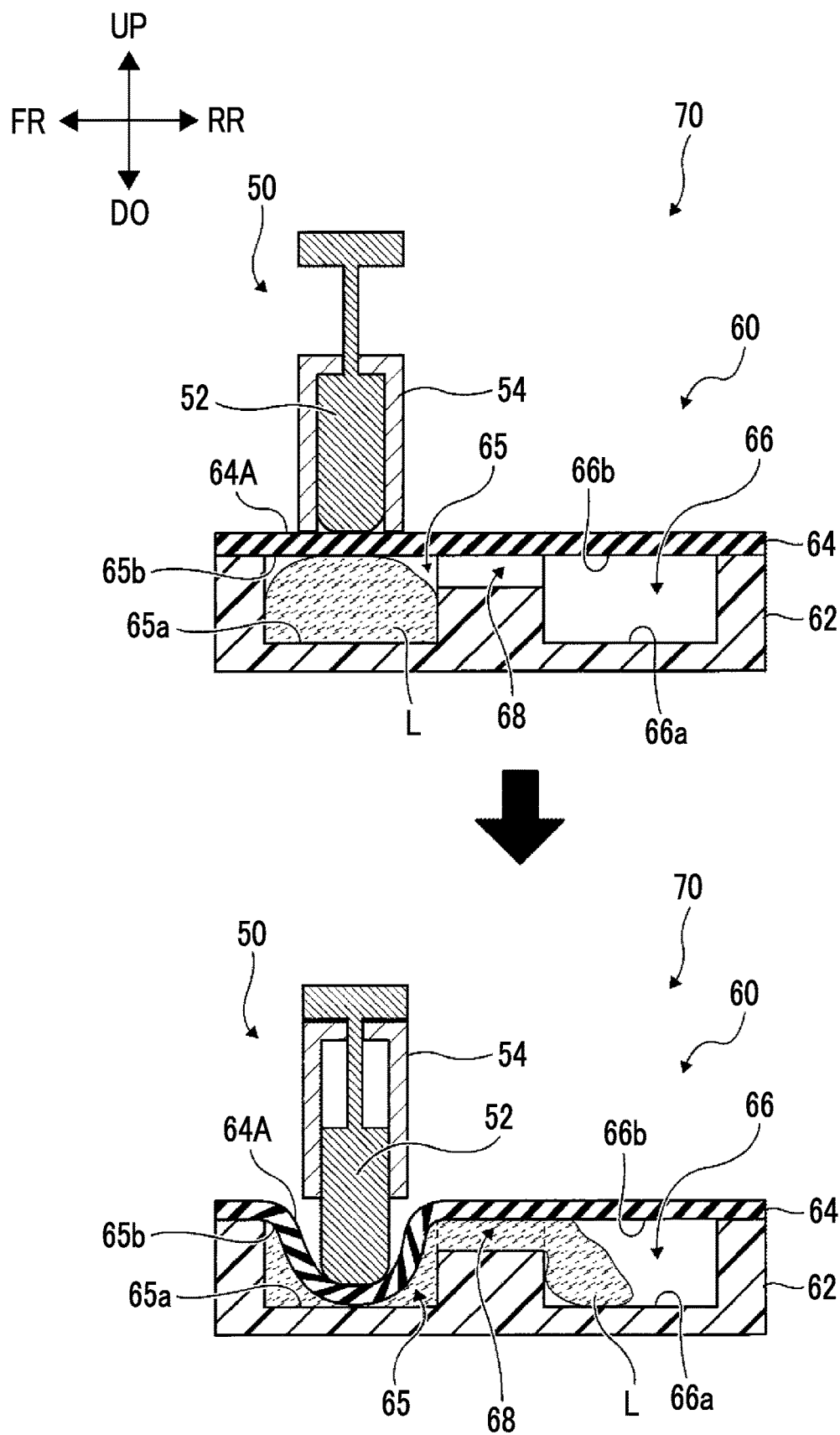
FIG. 3 is a diagram showing a liquid feeding method of the test container 60.
Figure 4:
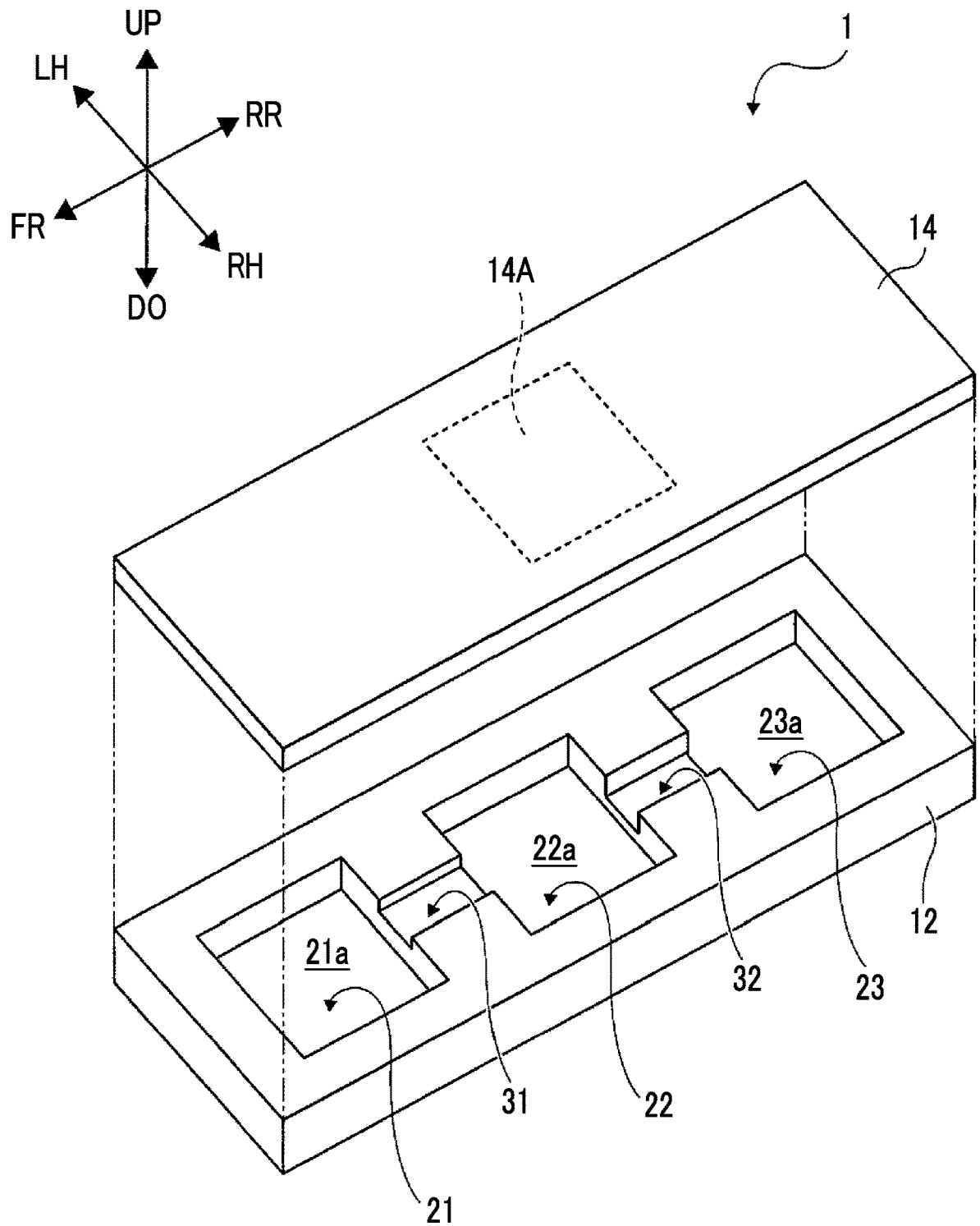
FIG. 4 is an exploded perspective view showing a schematic configuration of a test container 1.

A method for feeding a liquid of the test container 60 will be described together with a schematic configuration of a liquid feeding device 70 including the test container 60. FIG. 3 is a diagram for explaining a schematic configuration of the liquid feeding device 70 and a liquid feeding method. The liquid feeding device 70 includes a test container 60 and a pressing machine 50 including a plunger 52 as a pressing portion.

The pressing machine 50 presses the portion 64A forming the upper wall surface 65b of the one accommodation portion 65 of the test container 60 toward the inside of the accommodation portion 65 using the plunger 52. In this example, the pressing machine 50 includes a cylinder 54 which guides the plunger 52 during the pressing operation.

As shown in the lower diagram of FIG. 3, the pressing machine 50 presses the portion 64A of the upper lid member 64 toward the inside of the accommodation portion 65, so that the flexible portion 64A is deformed to the accommodation portion 65 side. Accordingly, the volume of the accommodation portion 65 can be reduced and a liquid L in the accommodation portion 65 can be fed to the other accommodation portion 66. The pressing portion included in the pressing machine 50 is not limited to the plunger as long as it can press the portion 64A toward the inside of the accommodation portion 65, and a rod-shaped pressing indenter, a cylinder, or the like can be selected. In addition, as for a tip shape, it is possible to appropriately select a shape such as a cylinder, a prism, a hemisphere, a cone, a polygonal pyramid, a flat shape, or a wedge shape.

Since at least the portion 64A of the test container 60 is a flexible film having a breaking elongation of 100% to 600%, the portion 64A is pressed to extend from the outside towards the inside of the accommodation portion 65, to be deformed towards the inside of the accommodation portion 65, and accordingly, the liquid can be fed. In a case where the breaking elongation of the flexible film is 100% or more, the flexible film can be deformed without being broken and excellent liquid feeding can be performed. In addition, in a case where the breaking elongation of the flexible film is 600% or less, the flexible film is prevented from being bent in a case of manufacturing the test container, and a manufacturing yield is improved.

The breaking elongation of the flexible film is 100% to 600%, more preferably 200% to 500%, and even more preferably 200% to 400%.

In a case where a thickness of the flexible film is t μm, a modulus of elasticity of the flexible film is α MPa, and a depth of the one accommodation portion 65 is d μm,
relationships of $0.03 \leq t/d \leq 2.5$ and $2{,}000 \leq \alpha \times t \leq 250{,}000$ are preferably satisfied,
relationships of $0.03 \leq t/d \leq 1.8$ and $2{,}000 \leq \alpha \times t \leq 110{,}000$ are more preferably satisfied,
relationships of $0.08 \leq t/d \leq 1.0$ and $2{,}000 \leq \alpha \times t \leq 50{,}000$ are even more preferably satisfied, and
relationships of $0.2 \leq t/d \leq 0.4$ and $4{,}000 \leq \alpha \times t \leq 20{,}000$ are particularly preferably satisfied.

By setting the breaking elongation of the flexible film to be 100% to 600% and satisfying the relationships of $0.03 \leq t/d \leq 2.5$ and $2{,}000 \leq \alpha \times t \leq 250{,}000$, deformability of the upper lid is excellent which leads easy deformation, excellent followability with respect to indentation is obtained, and the liquid feeding properties can be further improved. In addition, by satisfying the relationships of $0.03 \leq t/d \leq 1.8$ and $2{,}000 \leq \alpha \times t \leq 110{,}000$, further satisfying the relationships of $0.08 \leq t/d \leq 1.0$ and $2{,}000 \leq \alpha \times t \leq 50{,}000$, and particularly satisfying the relationships of $0.2 \leq t/d \leq 0.4$ and $4{,}000 \leq \alpha \times t \leq 20{,}000$, the liquid feeding properties can be further improved.

As a material of the flexible film, a silicone resin, a fluororesin, polyolefin, polycarbonate, and the like are suitable.

A dispensing port for dispensing a liquid may be provided in a portion of the upper lid member 64 that forms each of the upper wall surfaces 65b and 66b of the accommodation portions 65 and 66. The dispensing port is opened at the time of dispensing but is preferably sealed at other times. Alternatively, the upper lid member 64 may be provided with no dispensing port, and the upper lid member 64 may be covered and adhered to an upper surface of the main body portion 62 after injecting the liquid to each of the accommodation portions 65 and 66.

As the material of the main body portion 62, any known resin-molded plastic materials can be used without particular limitation. Examples thereof include an acrylic resin such as a polymethyl methacrylate resin (PMMA), a polyolefin resin such as a polycarbonate resin, polyethylene (PE), polypropylene (PP), an ethylene-vinyl acetate copolymer (EVA), a cycloolefin resin such as a cycloolefin polymer (COP) and a cyclic olefin copolymer (COC), a silicone resin, a fluororesin, a polystyrene resin, a polyvinyl chloride resin, a phenol resin, a urethane resin, a polyester resin, an epoxy resin, and a cellulose resin. Particularly, from viewpoints of heat resistance and transparency, a polycarbonate resin, polypropylene, a cycloolefin resin, a silicone resin, and a fluororesin are preferable. In addition, a copolymer of these resins may be used.

A size (volume) of the accommodation portions 65 and 66 is, for example, approximately 1 μL (microliter) to several hundreds μL.

The test container 60 of the embodiment of the embodiment includes two accommodation portions, but the test container of the present disclosure may include three or more accommodation portions.

In a case where the test container includes a first accommodation portion; a second accommodation portion, a third accommodation portion, a first flow path connecting the first accommodation portion and the second accommodation portion to each other at respective upper end positions thereof, and a second flow path connecting the second accommodation portion and the third accommodation portion to each other at respective upper end positions thereof, it is more preferable to provide the test container including the liquid return prevention structure which prevents a backflow of the liquid to the first accommodation portion, in a case where the liquid accommodated in the second accommodation portion is fed to the third accommodation portion via the second flow path. The test containers 1 to 6 will be described below as an example having a liquid return prevention structure.

Test Container 1

Figure 5:
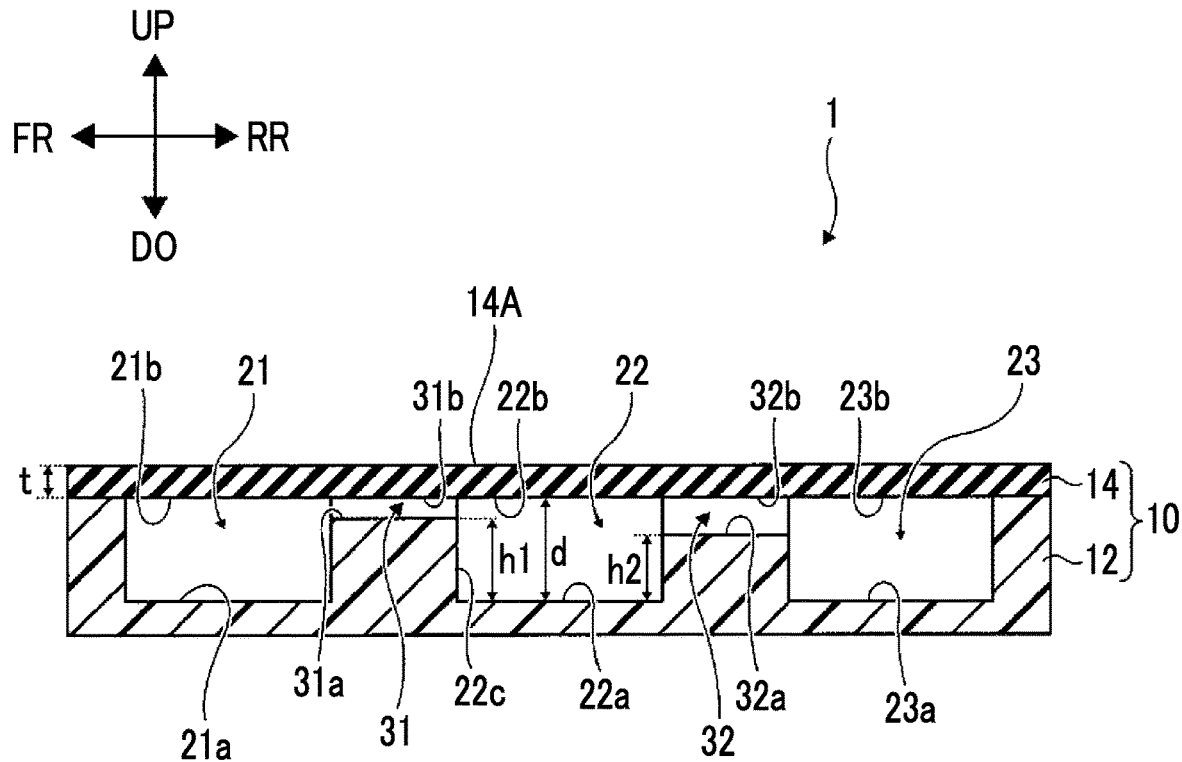
FIG. 5 is a cross-sectional view showing a schematic configuration of the test container 1.

The test container 1 will be described. FIG. 5 is a cross-sectional view showing a schematic configuration of the test container 1. The test container 1 shown in FIG. 1, FIG. 2, and FIG. 3 includes a container main body 10 being internally provided with a first accommodation portion 21, a second accommodation portion 22, and a third accommodation portion 23 each capable of accommodating a liquid, a first flow path 31 connecting the first accommodation portion 21 and the second accommodation portion 22 to each other at respective upper end positions thereof, and a second flow path connecting the second accommodation portion 22 and the third accommodation portion 23 to each other at respective upper end positions thereof. The second accommodation portion 22 corresponds to the one accommodation portion, and the third accommodation portion 23 corresponds to the other accommodation portion. The container main body 10 consists of a flexible film deformable inwards of the second accommodation portion 22 on at least a portion 14A forming an upper wall surface 22b of the second accommodation portion 22. In the test container 1, the liquid accommodated in the second accommodation portion 22 is fed to the third accommodation portion 23 via the flow path 32 due to deformation of the flexible film towards the second accommodation portion 22. Here, a breaking elongation of the flexible film is 100% to 600%.

In this example, the container main body 10 includes a main body portion 12 and an upper lid member 14. The main body portion 12 has an opening in a portion forming each of the first accommodation portion 21, the first flow path 31, the second accommodation portion 22, the second flow path 32, and the third accommodation portion 23. The container main body 10 has a configuration in which the first accommodation portion 21, the first flow path 31, the second accommodation portion 22, the second flow path 32, and the third accommodation portion 23 are formed therein by covering the opening of the main body portion 12 with the upper lid member 14. In other words, the main body portion 12 configures the inner bottom surfaces 21a to 23a and the side wall surfaces of the accommodation portions 21 to 23, and the inner bottom surfaces 31a and 32a and the side wall surfaces of the flow paths 31 and 32, and the upper lid member 14 configures the upper wall surfaces 21b to 23b of the accommodation portions 21 to 23 and the upper wall surfaces 31b and 32b of the flow paths 31 and 32. However, the present invention is not limited to this configuration, as long as it has a configuration of including each accommodation portion and each flow path therein.

In this example, the upper lid member 14 has flexibility throughout. However, the entire upper lid member 14 does not have to be flexible, as long as the portion 14A configuring at least the upper wall surface 22b of the second accommodation portion 22 of the container main body 10, that is, the portion 14A of the upper lid member 14 has a flexible portion deformable in a direction toward the second accommodation portion 22. Regarding physical properties such as the breaking elongation and the modulus of elasticity of the flexible film, the thickness, and the like, the same as those described in the above embodiment can be used, and the same effect can be obtained.

As a liquid return prevention structure, the test container 1 has a structure in which a height h1 from the inner bottom surface 22a of the second accommodation portion 22 to the inner bottom surface 31a of the first flow path 31 (hereinafter, referred to as a "height h1 of the first flow path") is higher than a height h2 from the inner bottom surface 22a of the second accommodation portion 22 to the inner bottom surface 32a of the second flow path 32 (hereinafter, referred to as a "height h2 of the second flow path"). In the test container 1, the height h1 of the inner bottom surface 31a of the first flow path 31 from the inner bottom surface 22a of the second accommodation portion 22 is defined as a height of a corner of a level difference portion between the first flow path 31 and the second accommodation portion 22 from the inner bottom surface 22a of the second accommodation portion 22. In the same manner, the height h2 of the inner bottom surface 32a of the second flow path 32 from the inner bottom surface 22a of the second accommodation portion 22 is defined as a height of a corner of a level difference portion between the second accommodation portion 22 and the second flow path 32 from the inner bottom surface 22a of the second accommodation portion 22. The liquid return prevention structure is a structure for preventing a backflow of the liquid to the first accommodation portion 21, in a case where the liquid accommodated in the second accommodation portion 22 is fed to the third accommodation portion 23 via the second flow path 32 due to the deformation of the portion 14A forming the upper wall surface 22b of the second accommodation portion 22 in a direction toward the second accommodation portion 22.

The test container 1 includes the first flow path 31 at the upper end position of the first accommodation portion 21 and the second accommodation portion 22, and the second flow path 32 at the upper end position of the second accommodation portion 22 and the third accommodation portion 23, respectively. Accordingly, the liquid accommodated in the accommodation portion is difficult to flow into the flow path, compared to a case where the flow path is included at a lower end or in the middle in a depth direction. Therefore, it is possible to prevent a passage of the liquid into the flow path due to a capillary phenomenon or the like without applying an external force. Meanwhile, since the portion 14A deformable toward the inside of the second accommodation portion 22 is included at the upper portion of the second accommodation portion 22, the portion 14A is deformed toward the inside of the second accommodation portion 22 to reduce a volume of the second accommodation portion 22, thereby easily realizing liquid feeding to the third accommodation portion 23 by pushing the liquid accommodated in the second accommodation portion 22. Here, since the portion 14A is a flexible film having a breaking elongation of 100% to 600%, the portion 14A is pressed to extend from the outside towards the inside of the second accommodation portion 22, to be deformed towards the inside of the second accommodation portion 22, and accordingly, the liquid can be fed. In a case where the breaking elongation of the flexible film is 100% or more, the flexible film can be deformed without being broken and excellent liquid feeding can be performed. In a case where the breaking elongation of the flexible film is 100% or more, the flexible film can be deformed without being broken and excellent liquid feeding can be performed. The same applies to test containers 2 to 6 below.

Since the height h1 of the first flow path 31 is higher than the height h2 of the second flow path 32, in a case where the portion 14A of the container main body 10 is deformed in the direction toward the second accommodation portion 22 so that the liquid accommodated in the second accommodation portion 22 is fed to the third accommodation portion 23 via the second flow path 32, the liquid pushed from the second accommodation portion 22 is preferentially fed to the second flow path 32 formed at a lower position. Accordingly, the liquid return to the first flow path 31 can be suppressed, and the liquid feeding properties to the third accommodation portion 23 at a downstream side is high. According to this configuration, it is possible to suppress the liquid return to the first flow path 31 and increase the liquid feeding properties to the third accommodation portion 23 with a simple configuration of providing a difference between the heights h1 and h2.

A difference h1−h2 between the height h1 of the first flow path 31 and the height h2 of the second flow path 32 is preferably 20% or more, more preferably 30% or more, and particularly preferably 50% or more of the height h2 of the second flow path 32. As the difference h1−h2 is large, the liquid feeding to the second flow path 32 is further promoted, and the liquid feeding properties to the third accommodation portion 23 can be increased.

In the test container 1, a corner formed by an inner bottom surface 31a of the first flow path 31 and an inner side surface 22c of the second accommodation portion 22 in a level difference portion between the inner bottom surface 31a of the first flow path 31 and the second accommodation portion 22 preferably has an acute angle. By setting the corner of the level difference portion to have an acute angle, it is possible to more effectively suppress the flow of the liquid accommodated in the second accommodation portion 22 to the first flow path 31, compared to a case where the angle is equal to or greater than 90°. Therefore, it is possible to more preferentially feed the liquid accommodated in the second accommodation portion 22 to the second flow path 32.

Test Container 2

Figure 6:
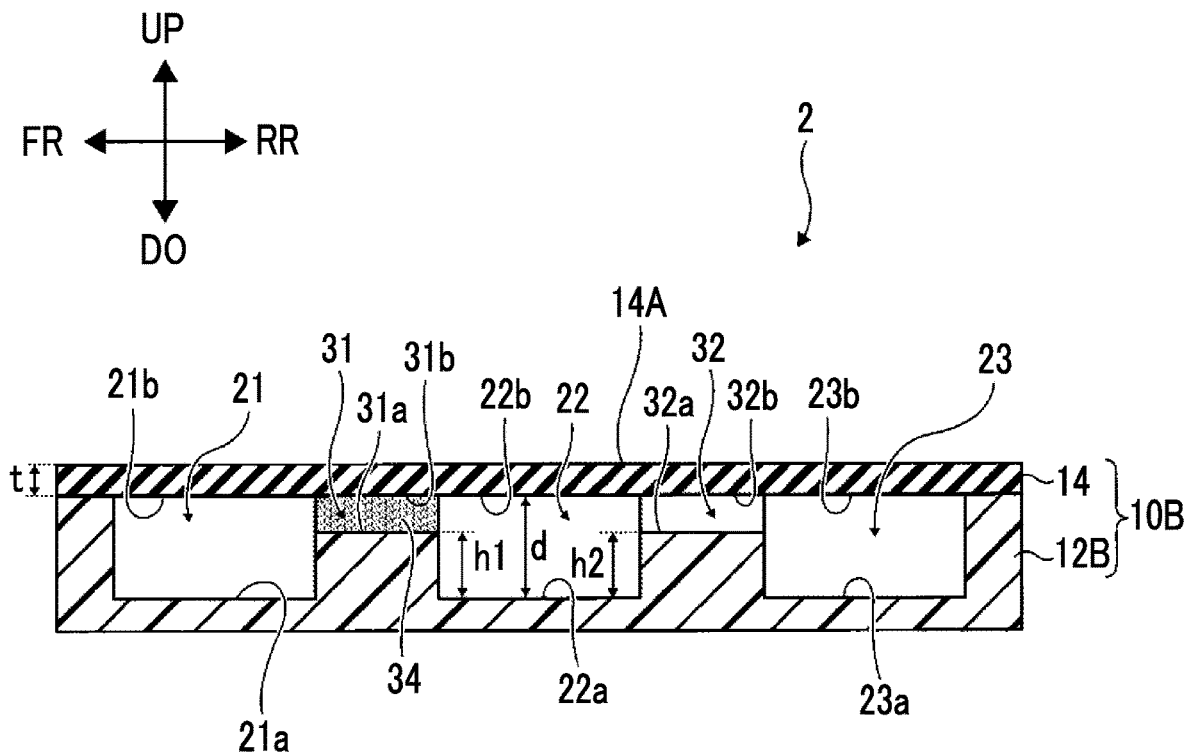
FIG. 6 is a cross-sectional view showing a schematic configuration of the test container 2.

The test container 2 will be described. FIG. 6 is a cross-sectional view showing a schematic configuration of the test container 2. The test container 2 includes a container main body 10B being internally provided with the first accommodation portion 21, the second accommodation portion 22, and the third accommodation portion 23 each capable of accommodating a liquid, the first flow path 31 connecting the first accommodation portion 21 and the second accommodation portion 22 to each other at respective upper end positions thereof, and the second flow path 32 connecting the second accommodation portion 22 and the third accommodation portion 23 to each other at respective upper end positions thereof. The container main body 10B has at least the portion 14A forming the upper wall surface 22b of the second accommodation portion 22 having flexibility to be deformable inwards of the second accommodation portion 22. In the drawings, the same reference numerals are used for the same elements as those of the test container 1. Elements having the same reference numerals as those of the test container 1 are the same as those described for the test container 1, and specific description thereof will be omitted. The same applies to the following drawings.

In this example, the container main body 10B includes the main body portion 12B and the upper lid member 14. The main body portion 12B has an opening in a portion forming each of the first accommodation portion 21, the first flow path 31, the second accommodation portion 22, the second flow path 32, and the third accommodation portion 23. The container main body 10B has a configuration in which the first accommodation portion 21, the first flow path 31, the second accommodation portion 22, the second flow path 32, and the third accommodation portion 23 are formed therein by covering the opening of the main body portion 12B with the upper lid member 14. In other words, the main body portion 12B configures the inner bottom surfaces 21a to 23a and the side wall surfaces of the accommodation portions 21 to 23, and the inner bottom surfaces 31a and 32a and the side wall surfaces of the flow paths 31 and 32, and the upper lid member 14 configures the upper wall surfaces 21b to 23b of the accommodation portions 21 to 23 and the upper wall surfaces 31b and 32b of the flow paths 31 and 32. However, the present invention is not limited to this configuration, as long as it has a configuration of including each accommodation portion and each flow path therein.

The test container 2 has a structure of the first flow path 31 and the second flow path 32 in which a water contact angle R1 of the inner surface of the first flow path 31 is set to be greater than a water contact angle R2 of the inner surface of the second flow path 32, as the liquid return prevention structure. In this example, a hydrophobic surface 34 obtained by performing a hydrophobic treatment is formed on the inner surface of the first flow path 31.

In order to generate a difference in a water contact angle between the inner surface of the first flow path 31 and the inner surface of the second flow path 32, the hydrophobic treatment may be performed on the inner surface of the first flow path 31 as in this example and/or a hydrophilic treatment may be performed on the inner surface of the second flow path 32.

In the test container 2, the portion 14A of the container main body 10B is deformed in the direction toward the second accommodation portion 22, so that the liquid accommodated in the second accommodation portion 22 is fed to the third accommodation portion 23 via the second flow path 32. In this case, since the water contact angle of the inner surface of the first flow path 31 is greater than the water contact angle of the inner surface of the second flow path 32, the liquid pushed from the second accommodation portion 22 is preferentially fed to the second flow path 32 having a smaller water contact angle. Accordingly, the liquid return to the first flow path 31 can be suppressed, and the liquid feeding properties to the third accommodation portion 23 at a downstream side is high. According to this configuration, it is possible to suppress the liquid return to the first flow path 31 and increase the liquid feeding properties to the third accommodation portion 23 with a simple process of only the surface treatment.

The surface treatment such as the hydrophilic treatment or the hydrophobic treatment is preferably formed on the entire inner surface of each flow path, but a part of the inner surface may not be treated.

Examples of the hydrophilic treatment include a surface modification treatment such as a corona treatment, a plasma treatment, an ozone treatment, a treatment of applying a hydrophilic coating agent, and bonding of a hydrophilic film. Examples of the hydrophobic treatment include a treatment of applying a hydrophobic coating agent such as a fluororesin or a hydrophobic silica-containing resin, a silane coupling treatment, and bonding of a water-repellent film.

A difference R1−R2 between the water contact angle R1 of the first flow path 31 and the water contact angle R2 of the second flow path 32 is preferably 10° or more, more preferably 20° or more, even more preferably 40° or more, and further preferably 60° or more.

In the present specification, the water contact angle is a contact angle of pure water. Specifically, 1 μL of pure water is added dropwise to the inner surface of the flow path and the accommodation portion under the condition of an atmosphere temperature of 25° C., the contact angle is measured by the θ/2 method using a fully-automatic contact angle meter (model number: DM-701, Kyowa Interface Science Co., Ltd.), and an arithmetic mean value of values obtained by measuring 5 times is used.

Test Container 3

Figure 7:
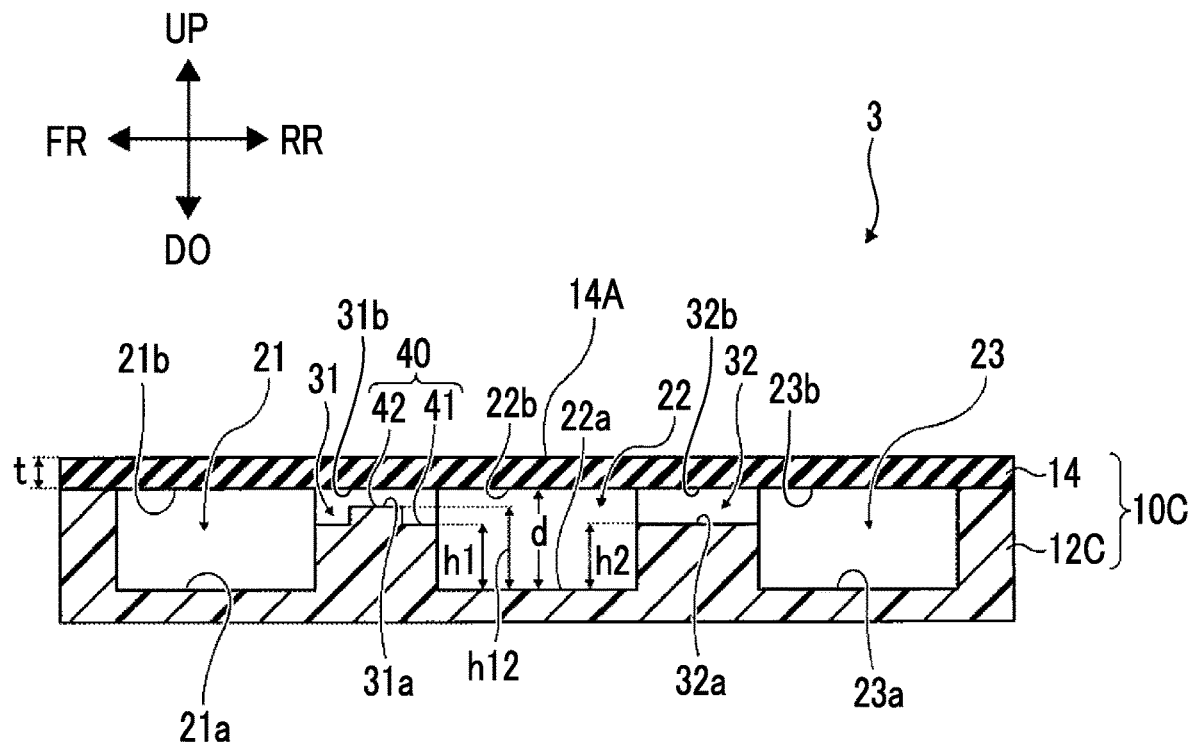
FIG. 7 is a cross-sectional view showing a schematic configuration of the test container 3.

The test container 3 will be described. FIG. 7 is a cross-sectional view showing a schematic configuration of the test container 3. The test container 3 includes the container main body 10C being internally provided with the first accommodation portion 21, the second accommodation portion 22, and the third accommodation portion 23 each capable of accommodating a liquid, the first flow path 31 connecting the first accommodation portion 21 and the second accommodation portion 22 to each other at respective upper end positions thereof, and the second flow path 32 connecting the second accommodation portion 22 and the third accommodation portion 23 to each other at respective upper end positions thereof. The container main body 10C has at least the portion 14A forming the upper wall surface 22b of the second accommodation portion 22 having flexibility to be deformable inwards of the second accommodation portion 22.

In this example, the container main body 10C includes the main body portion 12C and the upper lid member 14. The main body portion 12C has an opening in a portion forming each of the first accommodation portion 21, the first flow path 31, the second accommodation portion 22, the second flow path 32, and the third accommodation portion 23. The container main body 10C has a configuration in which the first accommodation portion 21, the first flow path 31, the second accommodation portion 22, the second flow path 32, and the third accommodation portion 23 are formed therein by covering the opening of the main body portion 12C with the upper lid member 14. That is, the main body portion 12C constitutes the inner bottom surfaces 21a to 23a and the side wall surfaces of the accommodation portions 21 to 23, and the inner bottom surfaces 31a and 32a and the side wall surfaces of the flow paths 31 and 32, respectively. The upper lid member 14 configures the upper wall surfaces 21b to 23b of the accommodation portions 21 to 23 and the upper wall surfaces 31b and 32b of the flow paths 31 and 32. However, the present invention is not limited to this configuration, as long as it has a configuration of including each accommodation portion and each flow path therein.

The test container 3 has a structure of a stepped portion 40 which is provided on the second accommodation portion 22 side of the first flow path 31 and which includes two or more steps 41 and 42 from the inner bottom surface 22a of the second accommodation portion 22, as the liquid return prevention structure. On the other hand, the second flow path 32 does not include a stepped portion. In addition, in this example, the stepped portion is provided on the first accommodation portion 21 side of the first flow path 31, but the stepped portion may not be provided on the first accommodation portion 21 side.

In the test container 3, the portion 14A of the container main body 10C is deformed in the direction toward the second accommodation portion 22, so that the liquid accommodated in the second accommodation portion 22 is fed to the third accommodation portion 23 via the second flow path 32. In this case, since the first flow path 31 includes the stepped portion 40 having two or more steps, a barrier in a case where the liquid accommodated in the second accommodation portion 22 passes through the first flow path 31 has two or more steps. Accordingly, the invasion of the liquid into the first flow path 31 is suppressed, and the liquid pushed out from the second accommodation portion 22 is preferentially fed to the second flow path 32 having a smaller barrier. Therefore, the liquid return to the first flow path 31 is suppressed, and the liquid feeding properties to the third accommodation portion 23 at a downstream side is high. It is possible to obtain a high effect of preventing the liquid return to the first flow path 31 by providing the stepped portion 40 in the first flow path 31.

The stepped portion 40 includes a first step 41 on the second accommodation portion 22 side and a second step 42. The stepped portion 40 is not limited to two steps and may have three steps or four or more steps. However, from a viewpoint of avoiding complication of the structure, the stepped portion 40 preferably has two or three steps.

The height $h1$ of the first step 41 is preferably 25% or more, more preferably 30% or more, and even more preferably 50% or more of d, where d is a height (depth) from the inner bottom surface 22a to the upper wall surface 22b of the second accommodation portion 22.

A height $h12$ of the second step 42 is preferably 50% or more, more preferably 60% or more, and even more preferably 80% or more of the height d of the second accommodation portion 22. A difference between the height $h12$ of the second step 42 and the height $h1$ of the first step 41 is preferably 20% or more of the height $h1$ of the first step 41, from a viewpoint of preventing the liquid return. The height $h12$ of the second step 42 is defined as a height from the inner bottom surface 22a of the second accommodation portion 22 at the corner of the level difference portion with the first step 41.

In the test container 3, a corner formed by the inner bottom surface and the inner side surface forming at least one step of the stepped portion 40 preferably has an acute angle. By setting the corner of the level difference portion to have an acute angle, it is possible to more effectively suppress the flow of the liquid accommodated in the second accommodation portion 22 to the first flow path 31, compared to a case where the angle is equal to or greater than 90°. Therefore, it is possible to more preferentially feed the liquid accommodated in the second accommodation portion 22 to the second flow path 32.

As described above, the test container 1 includes a structure in which the height $h1$ of the first flow path 31 is higher than the height $h2$ of the second flow path 32 (hereinafter, referred to as a liquid return prevention structure 1). The test container 2 includes a structure of the first flow path 31 and the second flow path 32 in which the water contact angle of the inner surface of the first flow path 31 is set to be greater than the water contact angle of the inner surface of the second flow path 32 (hereinafter, referred to as a liquid return prevention structure 2). The test container 3 has a structure of the stepped portion 40 including two or more steps from the inner bottom surface 22a of the second accommodation portion 22 configured on the second accommodation portion 22 side of the first flow path 31 (hereinafter, referred to as a liquid return prevention structure 3).

Figure 8:
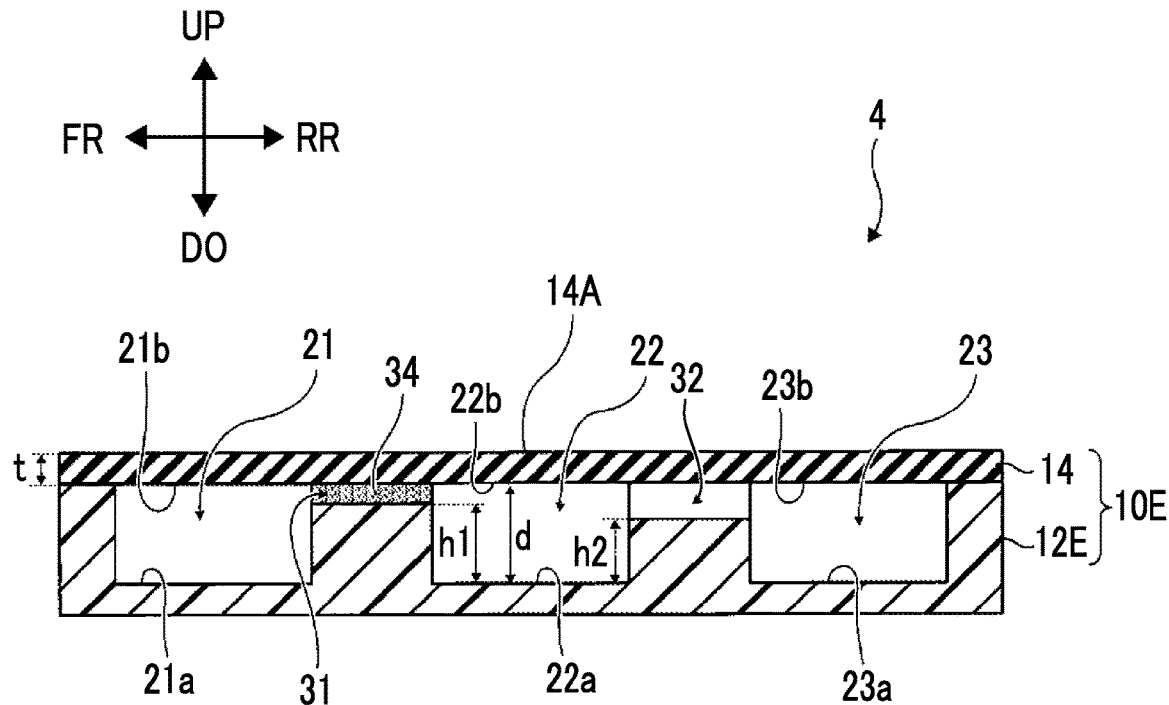
FIG. 8 is a cross-sectional view showing a schematic configuration of the test container 4.

It is also preferable to comprise these liquid return prevention structures 1 to 3 in combination. For example, as shown in FIG. 8, a test container 4 including the liquid return prevention structure 1 and the liquid return prevention structure 2 may be used. The test container 4 includes a container main body 10E formed of a main body portion 12E and the upper lid member 14. The test container 4 has a structure in which the height $h1$ of the first flow path and the height $h2$ of the second flow path satisfy a relationship of $h1>h2$ and includes the hydrophobic surface 34 obtained by performing a hydrophobic treatment on the inner surface of the first flow path 31, and the water contact angle of the inner surface of the first flow path 31 is higher than the water contact angle of the inner surface of the second flow path 32.

Figure 9:
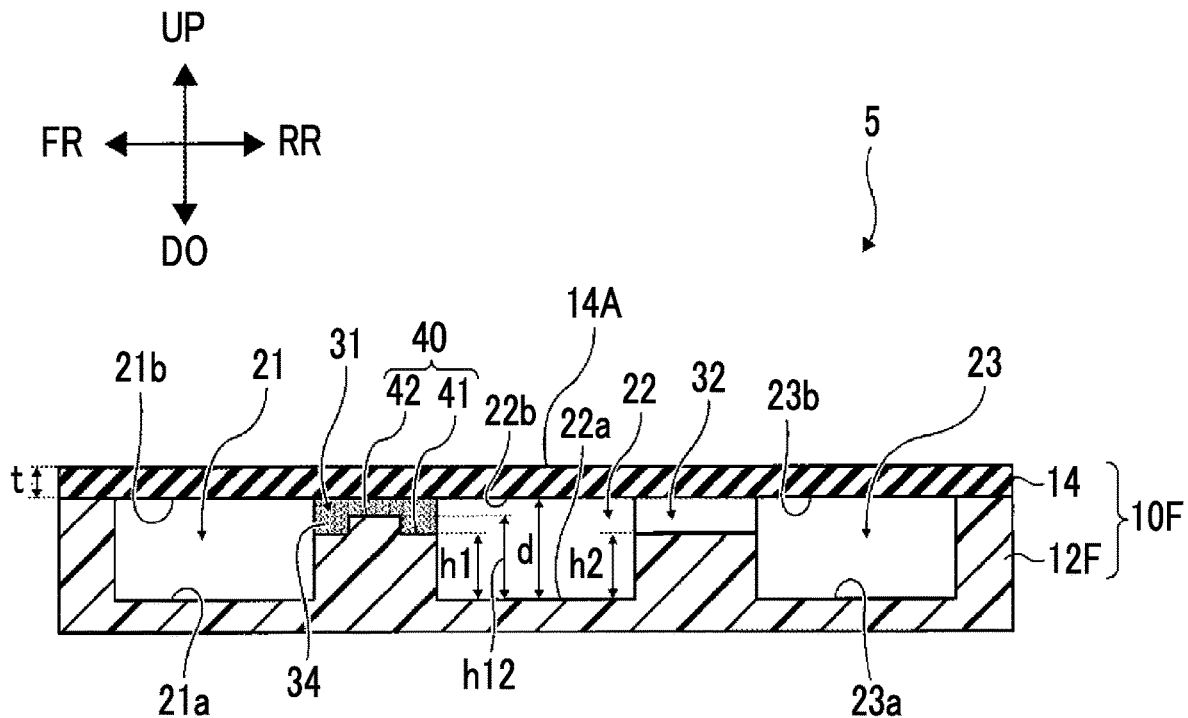
FIG. 9 is a cross-sectional view showing a schematic configuration of the test container 5.

As shown in FIG. 9, a test container 5 including the liquid return prevention structure 2 and the liquid return prevention structure 3 may be used. The test container 5 includes a container main body 10F forming of a main body portion 12F and the upper lid member 14. The test container 5 includes the hydrophobic surface 34 obtained by performing a hydrophobic treatment on the inner surface of the first flow path 31 and includes the stepped portion 40 in the first flow path 31, and the water contact angle of the inner surface of the first flow path 31 is higher than the water contact angle of the inner surface of the second flow path 32.

Figure 10:
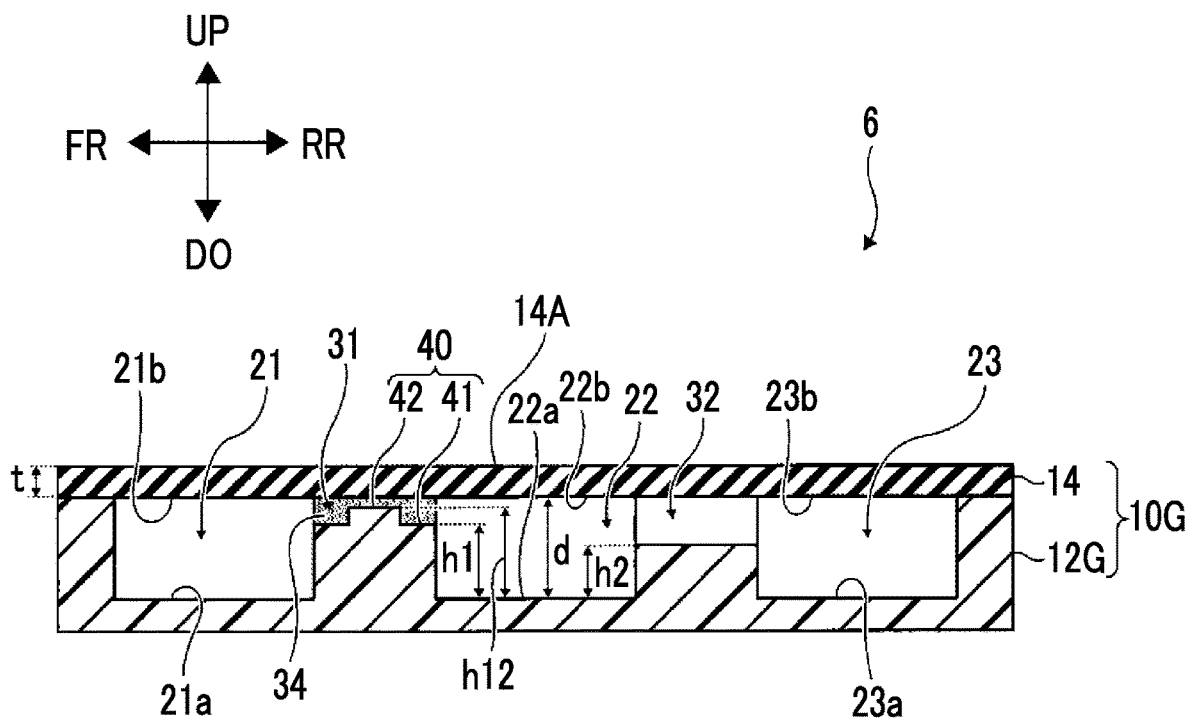
FIG. 10 is a cross-sectional view showing a schematic configuration of the test container 6.

In addition, the test container may be a test container including the liquid return prevention structure 1 and the liquid return prevention structure 3, or as shown in FIG. 10, a test container 6 including all the liquid return prevention structures 1 to 3. The test container 6 includes a container main body 10G formed of a main body portion 12G and the upper lid member 14. The test container 6 has a structure in which the height h1 of the first flow path 31 and the height h2 of the second flow path 32 satisfy a relationship of h1>h2 and includes the hydrophobic surface 34 obtained by performing a hydrophobic treatment on the inner surface of the first flow path 31, and the water contact angle of the inner surface of the first flow path 31 is higher than the water contact angle of the inner surface of the second flow path 32. In addition, the first flow path 31 includes the stepped portion 40.

According to the test container including two or three the liquid return prevention structures 1 to 3 in combination, it is possible to obtain a higher effect of the liquid return prevention, compared to a case of including only the liquid return prevention structure 1, only the liquid return prevention structure 2, or only the liquid return prevention structure 3.

In addition, the liquid return prevention structure is not limited to the above example, and the first flow path between the second accommodation portion and the first accommodation portion may have a structure in which the liquid accommodated in the second accommodation portion relatively hardly flows, compared to the second flow path between the second accommodation portion and the third accommodation portion. For example, a structure including a valve may be included in each of the first flow path and the second flow path may be provided as the liquid return prevention structure. In a case where a valve is provided in each of the first flow path and the second flow path, the liquid is fed in a state where the valve of the first flow path is closed and valve of the second flow path is opened, in a case of feeding the liquid from the second accommodation portion to the third accommodation portion, it is possible to effectively prevent the liquid return to the first accommodation portion and improve the liquid feeding properties to the third accommodation portion.

Application Example to Nucleic Acid Extraction Test

The test container according to the embodiment of the technology of the present disclosure can be applied as, for example, a test cartridge for a nucleic acid extraction test. A nucleic acid extraction test using a test container 101 according to another embodiment of the technology of the present disclosure will be described.

Figure 11:
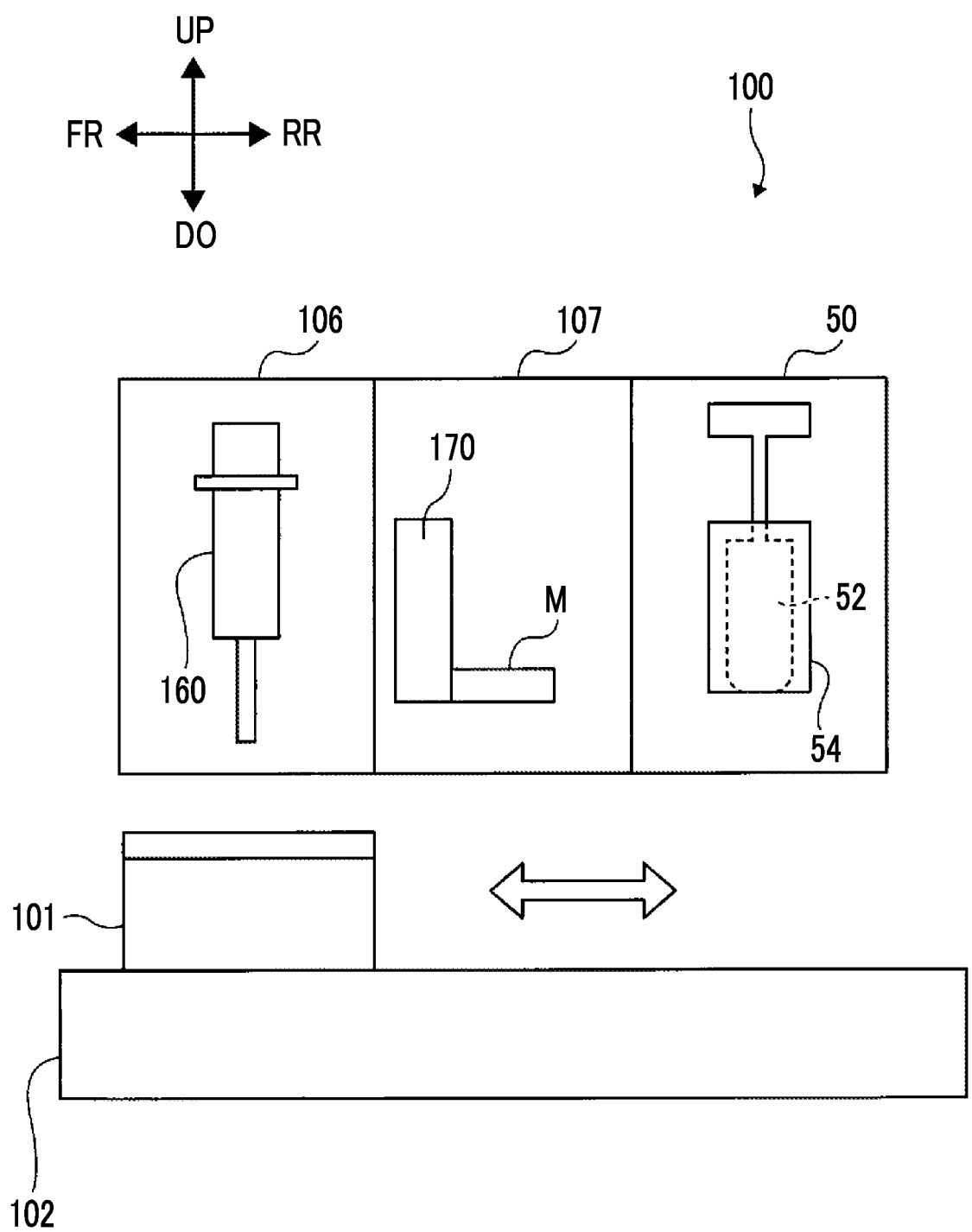
FIG. 11 is a schematic configuration diagram of a nucleic acid extraction test device 100.

FIG. 11 is a configuration diagram showing a schematic configuration of a nucleic acid extraction test device 100 including the test container 101. The nucleic acid extraction test device 100 includes the test container 101, the pressing machine 50, a dispenser 106, a magnetic field generation and movement unit 107, and a transfer portion 102 for the test container 101.

Figure 12:
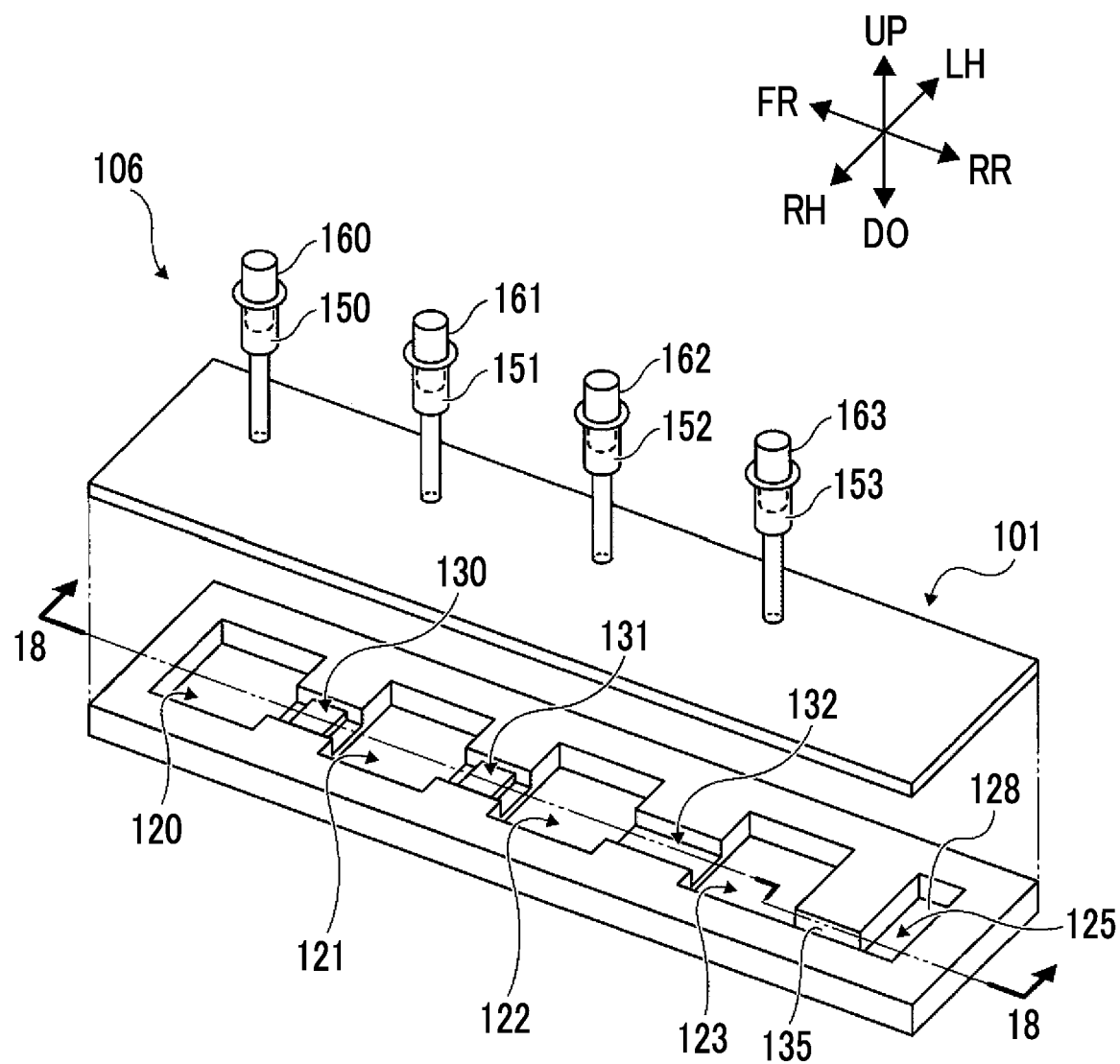
FIG. 12 is an exploded perspective view of a test container and a diagram showing a main part of a dispenser.
Figure 13:
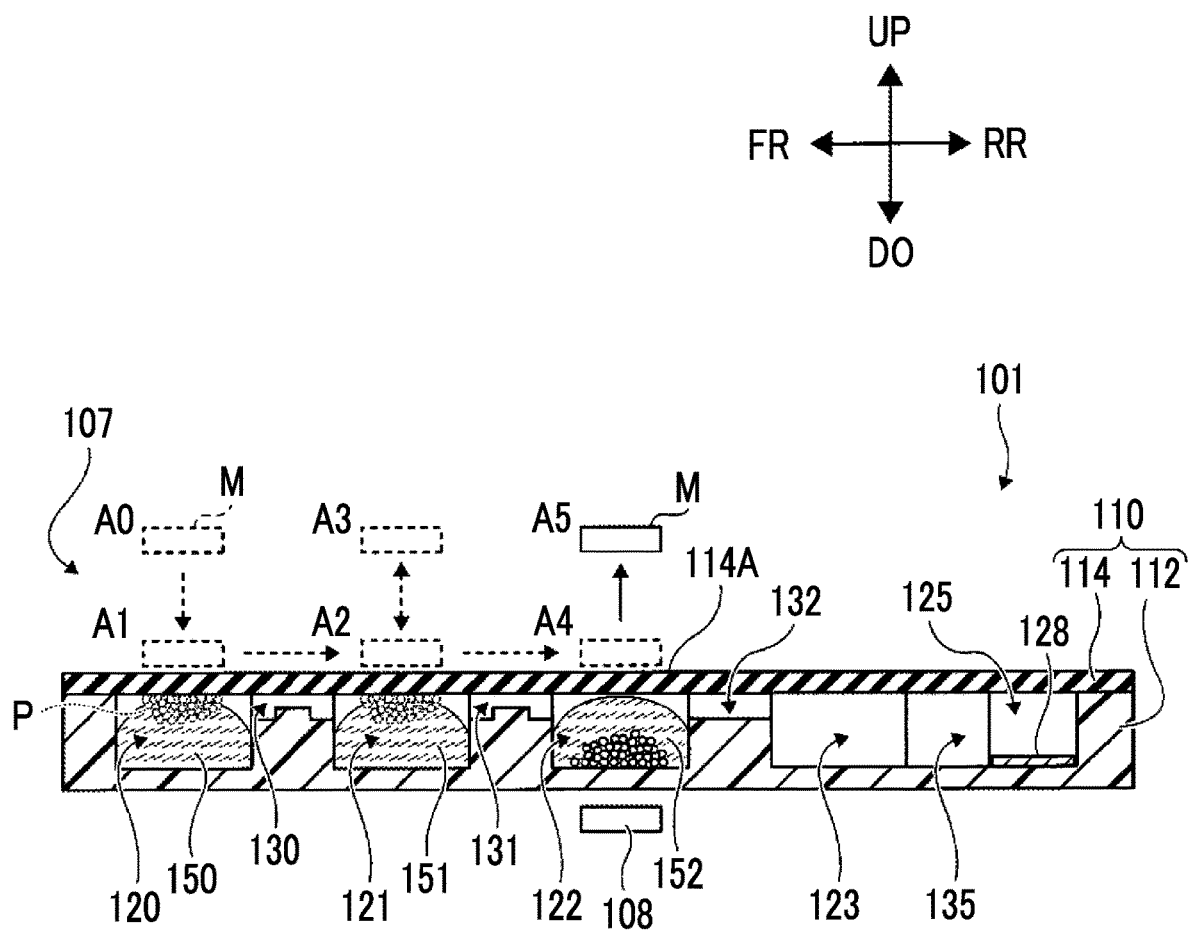
FIG. 13 is a diagram showing a cross-sectional view of a test container and a magnet.
Figure 14:
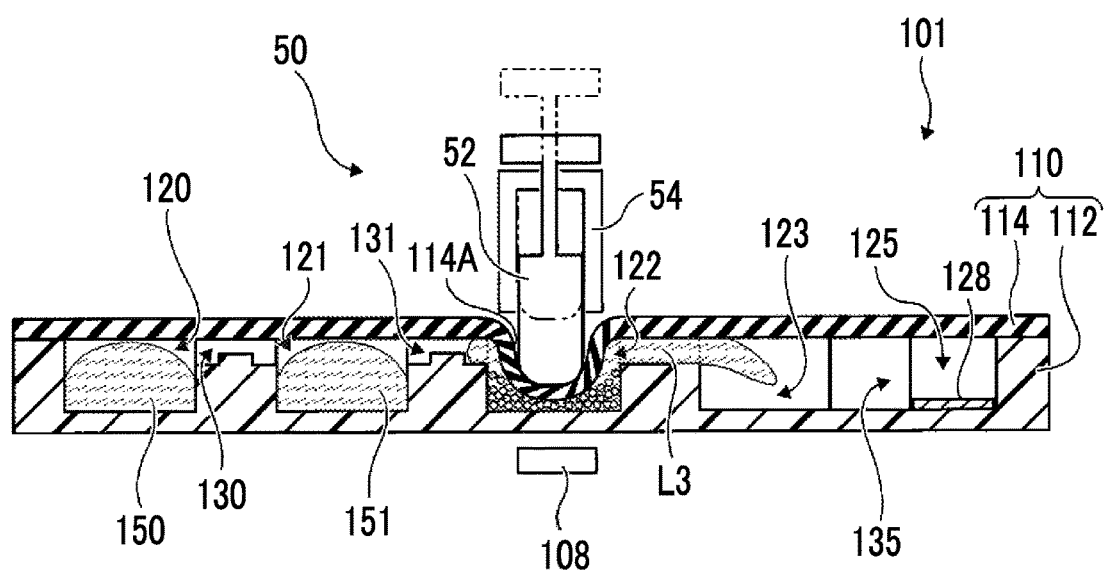
FIG. 14 is a diagram showing a cross-sectional view of a test container and a main part of a pressing machine.

FIG. 12 is an exploded perspective view of the test container 101 and a diagram showing a main part of the dispenser 106. FIG. 13 is a diagram showing the test container 101 and a magnet M of the magnetic field generation and movement unit 107. FIG. 14 is a diagram showing the test container 101 and a main part of the pressing machine 50. FIGS. 13 and 14 show cross-sectional views taken along a line 18-18 of the test container 101 shown in FIG. 12.

The test container 101 includes a container main body 110 being internally provided with four accommodation portions 120 to 123 capable of accommodating a liquid, respectively, a chromatographic carrier accommodation portion 125 accommodating a chromatographic carrier 128, and four flow paths 130, 131, 132, and 135 therein.

The container main body 110 includes a main body portion 112 and an upper lid member 114. The main body portion 112 has an opening in a portion forming each of the accommodation portions 120 to 123 and 125 and the flow paths 130, 131, 132, and 135. The container main body 110 has a configuration in which the accommodation portions 120 to 123 and 125 and the flow paths 130, 131, 132, and 135 are formed therein by covering the main body portion 112 with the upper lid member 114. The main body portion 112 configures the side wall surface and the bottom surface of each of the accommodation portions and the flow paths, and the upper lid member 114 configures the upper wall surface of each of the accommodation portions and the flow paths. In this example, the upper lid member 114 is formed of a flexible film. The upper lid member 114 is provided with an injection port (not shown) for injecting the liquid accommodated in each of the accommodation portions 120 to 123. The tips of syringes 160 to 163 are inserted into the injection ports, respectively, and various liquids can be injected into the corresponding accommodation portions 120 to 123.

The accommodation portion 120 is a magnetic particle collecting chamber (hereinafter, referred to as the magnetism collecting chamber 120) which accommodates a specimen solution 150 containing magnetic particles P to which a nucleic acid is adsorbed. The accommodation portion 121 is a cleaning chamber (hereinafter, referred to as a cleaning chamber 121) which accommodates a cleaning solution 151 and cleans a substance non-specifically adsorbed to the magnetic particles P. The accommodation portion 122 is a PCR chamber (hereinafter, referred to as a PCR chamber 122) which accommodates a polymerase chain reaction (PCR) solution 152. The accommodation portion 123 is a detection chamber (hereinafter, referred to as a detection chamber 123) for mixing an amplified nucleic acid and a development solution 153.

The flow path 130 connects a magnetism collecting chamber 120 and the cleaning chamber 121 to each other at respective upper end positions thereof. The flow path 130 includes a stepped portion on the sides of the magnetism collecting chamber 120 and the cleaning chamber 121, to suppress the flow of the specimen solution 150 accommodated in the magnetism collecting chamber 120 to the flow path 130 and to prevent the mixing of the specimen solution 150 with the cleaning solution 151 accommodated in the cleaning chamber 121.

The flow path 131 connects the cleaning chamber 121 and the PCR chamber 122 to each other at respective upper end positions thereof and the flow path 132 connects the PCR chamber 122 and the detection chamber 123 to each other at respective upper end positions thereof. The cleaning chamber 121, the PCR chamber 122, the detection chamber 123, and the flow paths 131 and 132 correspond to the first accommodation portion, the second accommodation portion, the third accommodation portion, the first flow path, and the second flow path in the technology of the present disclosure, respectively. In addition, here, the liquid return prevention structure of suppressing the backflow of the liquid to the cleaning chamber 121, in a case of feeding the liquid accommodated in the PCR chamber 122 to the detection chamber 123 through the flow path 132 may be included. In this example, the liquid return prevention structure 3 is included as the liquid return prevention structure. That is, as the liquid return prevention structure, a structure of a stepped portion including two or more steps from an inner bottom surface 122a of the PCR chamber 122, which is formed on the PCR chamber 122 side of the flow path 131, is included.

The liquid return prevention structure may include a structure (liquid return prevention structure 1) in which a height of the first flow path (flow path 131) is higher than a height of the second flow path (flow path 132). In addition, a structure of the first flow path and the second flow path in which the water contact angle of the inner surface of the first flow path is set to be greater than the water contact angle of the inner surface of the second flow path (liquid return prevention structure 2) may be included. Alternatively, two or more of other liquid return prevention structures and liquid return prevention structures 1 to 3 may be provided in combination.

The flow path 132 connects the PCR chamber 122 and the detection chamber 123 to each other at respective upper end positions thereof. The flow path 132 may include a valve (not shown), in order to prevent evaporation of the liquid in a case of adjusting a temperature of the PCR chamber. The valve may be any valve that can be opened in a case where liquid is fed from the PCR chamber 122 to the detection chamber 123.

The flow path 135 connects the detection chamber 123 and the chromatographic carrier accommodation portion 125 to each other at a lower end position.

The magnetic particles P are particles that are attracted by magnetic force. The magnetic particles P are, for example, magnetic particles processed so as to adsorb a specific sample such as DNA. Specifically, as the magnetic particles P, model number: Magnosphere MX100/Carboxyl and model number: Magnosphere MS160/Tosyl manufactured by JSR Corporation, sicastar manufactured by Corefront, Magrapid manufactured by Sanyo Chemical Industries, Ltd. can be used.

As the magnetic particles P, magnetic particles having a particle size in a range of 0.01 μm to 100 μm are used. As the magnetic particles P, magnetic particles having a particle size of approximately 1 μm to 10 μm are preferably used. The magnetic particles P may be included in the magnetism collecting chamber 120 in advance, or may be injected into the magnetism collecting chamber 120 together with the specimen solution 150.

The specimen solution 150 is, for example, a specimen solution containing a nucleic acid extracted from a specimen. The specimen solution 150 may include a surfactant for extracting a nucleic acid such as deoxyribonucleic acid (DNA) and ribonucleic acid (RNA) from the specimen and adsorbing the nucleic acid on the surfaces of the magnetic particles P. In addition, as the surfactant, for example, sodium dodecyl sulfate, polyoxyethylene sorbitan monolaurate (Tween 20), Triton X-100, or the like can be used. These surfactants may be used alone or in combination of a plurality thereof. A chaotropic substance such as guanidine hydrochloride may be included in order to promote extraction of nucleic acid from the specimen and surface adsorption to the magnetic particles P. In addition, instead of containing the surfactant, a nucleic acid extracted from a specimen using a column may be contained. In addition, a surfactant for suppressing aggregation of the magnetic particles P may be included.

The cleaning solution 151 removes the substance non-specifically adsorbed to the magnetic particles P. As the cleaning solution 151, water or a buffer solution, an organic solvent such as ethanol and isopropyl alcohol, or the like can be used. In a case where the buffer solution is used as the cleaning solution, salt is not particularly limited, but salt of tris or phosphoric acid is preferably used. In addition, in order to suppress the elution of RNA in the cleaning step, the surfactant such as sodium dodecyl sulfate, Triton X-100, or the like may be contained.

The PCR solution 152 is a solution for performing a process for amplifying nucleic acid by PCR. The PCR solution 152 contains, for example, reverse transcriptase, dNTP in which four kinds of deoxyribonucleotide triphosphates are mixed, and a primer for reverse transcriptase. Transcriptase is an enzyme that synthesizes complementary deoxyribonucleic acid (cDNA) using a base sequence of RNA as a template.

The chromatographic carrier accommodation portion 125 accommodates the chromatographic carrier 128. In the chromatographic carrier accommodation portion 125, the development solution 153 containing the amplified nucleic acid is developed. The chromatographic carrier 128 is a nucleic acid chromatographic carrier and indicates whether or not the target nucleic acid is present in the development solution 153.

The dispenser 106 includes the syringes 160 to 163 for adding various liquids 150 to 153 to the respective accommodation portions 120 to 123 of the test container 101.

The pressing machine 50 includes a plunger 52 is configured to be able to press a region corresponding to the PCR chamber 122 of the container main body 110 (here, the upper lid member 114) by the plunger 52.

The magnetic field generation and movement unit 107 includes the magnet M and a movement mechanism 170 that moves the magnet M.

The magnet M is, for example, a permanent magnet, but may be an electromagnet. As shown in FIG. 13, the magnet M is freely moved between positions A0 to A5 of the test container 101 on the upper lid member 114. The positions A0, A3, and A5 are positions where a magnetic force does not act on the magnetic particles P accommodated in the test container 101, even in a case where the magnet M is disposed. The position A1 is a position on the magnetism collecting chamber 120 and is a position where a magnetic force acts on the magnetic particles P in the magnetism collecting chamber 120 in a case where the magnet M is disposed. The position A2 is a position on the cleaning chamber 121 and is a position where magnetic force acts on the magnetic particles P in the cleaning chamber 121 in a case where the magnet M is disposed. The position A4 is a position on the PCR chamber 122 and is a position where a magnetic force acts on the magnetic particles P in the PCR chamber 122 in a case where the magnet M is disposed.

In a case of moving the magnetic particles P from the magnetism collecting chamber 120 to the cleaning chamber 121, first, the magnet M is disposed at the position A1. In a case where the magnet M is disposed at the position A1, the magnetic particles P accommodated in the magnetism collecting chamber 120 are collected by the magnetic force of the magnet M and are attracted and collected at the position corresponding to the magnet M with the upper lid member 14 interposed therebetween. In a case where the magnet M is moved to the position A2 along the upper lid member 14 from this state, the magnetic particles P are separated from the specimen solution 150 and moved to the cleaning chamber 121 according to the movement of the magnet M. Then, in a case where the magnet M is moved to the position A3, the magnetic particles P are dispersed in the cleaning solution 151.

In the same manner, in a case of moving the magnetic particles P from the cleaning chamber 121 to the PCR chamber 122, first, the magnet M is disposed at the position A2. In a case where the magnet M is disposed at the position A2, the magnetic particles P accommodated in the cleaning chamber 121 are attracted and collected at the position corresponding to the magnet M with the upper lid member 14 interposed therebetween. In a case where the magnet M is moved to the position A4 along the upper lid member 14 from this state, the magnetic particles P are separated from the cleaning solution 151 and moved to the PCR chamber 122 along the movement of the magnet M. After that, in a case where the magnet M is moved to the position A5, the magnetic particles P are dispersed in the PCR solution 152.

The movement mechanism 170 has a function of allowing the magnet M to pass the upper portion of the flow path 130 from the position A1 on the magnetism collecting chamber 120, to pass the upper portion of the flow path 131 from the position A2 on the cleaning chamber 121, and to freely move to the position A4 on the PCR chamber 122. In addition, the movement mechanism 170 moves the magnet M to the positions A0, A3 and A5 where the magnetic force does not reach the inside of the chambers 120, 121 and 122.

The nucleic acid extraction test device 100 further includes a temperature control unit 108 (see FIG. 13). The temperature control unit 108 controls a temperature of the PCR solution in the PCR chamber 122. The temperature control unit 108 includes a heating unit such as a heater or a Peltier element for heating a solution, and a cooling unit such as a Peltier element, a fan, a heat sink, or a liquid cooling mechanism for cooling a solution. The temperature control unit 108 raises or lowers the temperature of the solution so that the temperature is adjusted to a suitable temperature in each step of a heat denaturation step, an annealing step, and an extension step in PCR.

A transportation unit 102 is a device that relatively moves the test container 101 relatively to the dispenser 106, the magnetic field generation and movement unit 107, and the pressing machine 50. The transportation unit 102 may transport only the test container 101, or move the respective positions of the dispenser 106, the magnetic field generation and movement unit 107, and the pressing machine 50 with respect to the test container 101.

Nucleic Acid Extraction Test Method

The steps of the nucleic acid extraction test in the nucleic acid extraction test device 100 including the test container 101 will be described.

Pretreatment (Adsorption Process)

A sample containing RNA is mixed with a solution containing a surfactant that dissolves a cell membrane and the magnetic particles P to adsorb the RNA to the magnetic particles P. The sample containing RNA is not particularly limited, as long as it contains the RNA such as a biological sample and virus. As necessary, impurities may be removed with a filter or the like.

Magnetization Collection Process

The specimen solution 150 containing the magnetic particles P having RNA adsorbed, which was obtained in the pretreatment, is injected into the magnetism collecting chamber 120 by the syringe 160. After that, the magnet M is set at the position A1 on the magnetism collecting chamber 120. Accordingly, the magnetic particles P accommodated in the magnetism collecting chamber 120 are attracted to the magnet M and are collected at a position corresponding to the magnet M on the upper surface to be in an aggregated state (see FIG. 13).

In the magnetism collecting chamber 120, the adsorption process and the magnetism collection process may be performed in time series.

Then, by moving the magnet M along the flow path 130, the magnetic particles P are separated from the specimen solution 150 and moved to the cleaning chamber 121.

Cleaning Step

In the cleaning chamber 121, the magnetic particles P adsorbed with RNA are cleaned with the cleaning solution 151 accommodated in the cleaning chamber 121. The cleaning chamber 121 may be filled with the cleaning solution 151 in advance, or the cleaning solution 151 may be injected after the magnetic particles P are moved. The magnet M is moved to the position (position A3) where the magnetic force does not affect the cleaning chamber 121 and the magnetic particles P are dispersed in the cleaning solution 151, thereby promoting the cleaning. By performing the cleaning, the substances other than RNA that are non-specifically bound to the magnetic particles P are removed.

Then, by returning the magnet M to the position A2 on the cleaning chamber 121, the magnetic particles P are collected again at the position corresponding to the magnet M on the upper surface, and the magnet M is moved to the position A4 on the PCR chamber 122 along the flow path 131, thereby separating the magnetic particles P from the cleaning solution 151 and moving the magnetic particles to the PCR chamber 122. After that, the magnet M is moved to the position A5 where the magnetic force does not affect the PCR chamber 122, so that the magnetic particles P are dispersed in the PCR solution 152.

PCR Process

In the PCR chamber 122, the RNA adsorbed to the magnetic particles P is eluted into the PCR solution 152, and the DNA amplification by PCR is performed. The cDNA is synthesized from the extracted RNA and the cDNA is amplified by PCR. In this case, the magnetic particles P sink to the inner bottom surface of the PCR chamber 122 due to gravity.

Liquid Feeding Process

After the PCR step, the solution containing the amplified cDNA in the PCR chamber 122 is fed to the detection chamber 123. The test container 101 includes the flow path 131 at the upper end position of the cleaning chamber 121 and the PCR chamber 122, and the flow path 132 at the upper end position of the PCR chamber 122 and the detection chamber 123, respectively. Accordingly, it is possible to prevent the passage of the solution 152 from the PCR chamber 122 to the flow paths 131 and 132 due to a capillary phenomenon or the like, before this liquid feeding process.

As shown in FIG. 14, in a case where the liquid is fed, the plunger 52 is positioned on the PCR chamber 122 and the plunger 52 is pushed down along the cylinder 54. A portion 114A of the flexible upper lid member 114 is pushed by the plunger 52 and pushed inwards of the PCR chamber 122. This reduces the volume of the PCR chamber 122, so that the liquid in the PCR chamber 122 is fed to the detection chamber 123 through the flow path. In this example, the flexible film is used as the upper lid member 114, and the flexible film has a breaking elongation of 100% to 600%. Accordingly, in a case where the portion 114A is pressed by the plunger 52, the flexible film can be deformed without being broken and excellent liquid feeding can be performed. In addition, since the return prevention structure is provided, most of the solution 152 in the PCR chamber 122 does not flow backward to the cleaning chamber 121 side, and a large amount of the solution extruded from the PCR chamber 122 can be fed to the detection chamber 123. In addition, since the flow path 132 is included at the upper end position of the PCR chamber 122, a supernatant portion of the PCR solution can be preferentially fed while the magnetic particles P are submerged on the inner bottom surface, and the magnetic particles P can be suppressed from flowing out to the detection chamber 123 side. By suppressing the magnetic particles P from flowing to the detection chamber 123, it is possible to perform a test with less noise in the next step.

Detection Process

In the detection chamber 123, the solution containing cDNA is mixed with the development solution. After that, the mixed liquid passes through the flow path 135 and is developed by the nucleic acid chromatographic carrier (chromatographic carrier 128) disposed in the chromatographic carrier accommodation portion 125. In a case where the RNA to be tested is contained, a positive result is obtained, and in a case where not, a negative result is obtained.

The nucleic acid extraction test is performed as described above.

Hereinabove, the case where the reverse transcription PCR method is used as the amplification method has been described, but the amplification method is not limited to the reverse transcription PCR method, and well-known amplification methods such as the transcription PCR method, the isothermal amplification method (for example, Nucleic Acid Sequence-Based Amplification (NASBA), Loop-mediated Isothermal Amplification (LAMP), transcription-reverse transcription concerted (TRC), and the like) can be used. In addition, hereinabove, the case where the nucleic acid chromatography method is used as the detection method has been described, but the detection method is not limited to the nucleic acid chromatography method, and well-known methods such as a fluorescence detection method (intercalator method, probe method, or the like), a light scattering method using gold nanoparticles, a sequence method, an electrochemical method, a piezoelectric method, and detection of a weight or a mechanical change can be used. In these cases, the container does not necessarily comprise the chromatographic carrier 128 and the accommodation portion 125 thereof. On the other hand, the test device may comprise a detection unit suitable for various detection methods of a fluorescence detection unit and the like for detecting fluorescence from the detection chamber 123. However, the nucleic acid chromatography method is preferable because a high-priced detection system and detection equipment are not necessary and the operation in the analysis is simple.

By using the test container 101, the solution containing the DNA amplified in the PCR chamber 122 can be efficiently fed to the detection chamber 123 while suppressing the backflow to the cleaning chamber 121, and a sufficient amount of solution to be fed can be realized. Since the backflow can be suppressed to increase the amount of liquid to be fed to the detection chamber 123, a total amount of DNA that flows into the detection chamber 123 can be increased, which leads to improvement in determination accuracy.

In regard to the test container 101, a set of the test container 101, the magnetic particles P, and various treatment liquids such as the cleaning solution 151, the PCR solution 152, and the development solution 153 can also be provided as a test kit. The test kit may further include other treatment liquid such as a nucleic acid eluate. In addition, as the test kit, it is also possible to provide a set of only the test container 101 and the magnetic particles P. The magnetic particles P may be set in the magnetism collecting chamber 120 of the test container 101 in advance, or may be separately prepared.

The technology of the present disclosure is not limited to the embodiment described above, and various modifications, changes, and improvements can be made without departing from the spirit of the invention. For example, the modification examples described above may be appropriately configured in combination.

EXAMPLES

Hereinafter, more specific examples and comparative examples of the technology of the present disclosure will be described.

Figure 15:
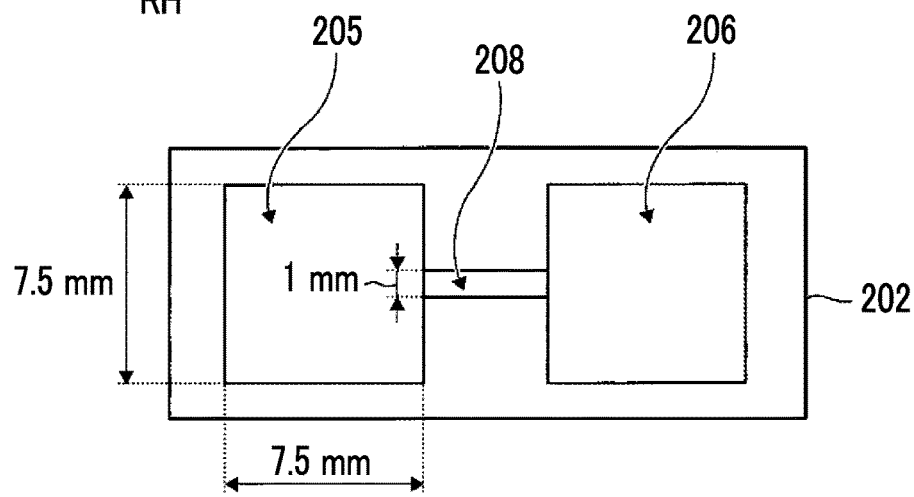
FIG. 15 is a plan view of a main body portion of the test container of examples and comparative examples.
Figure 16:
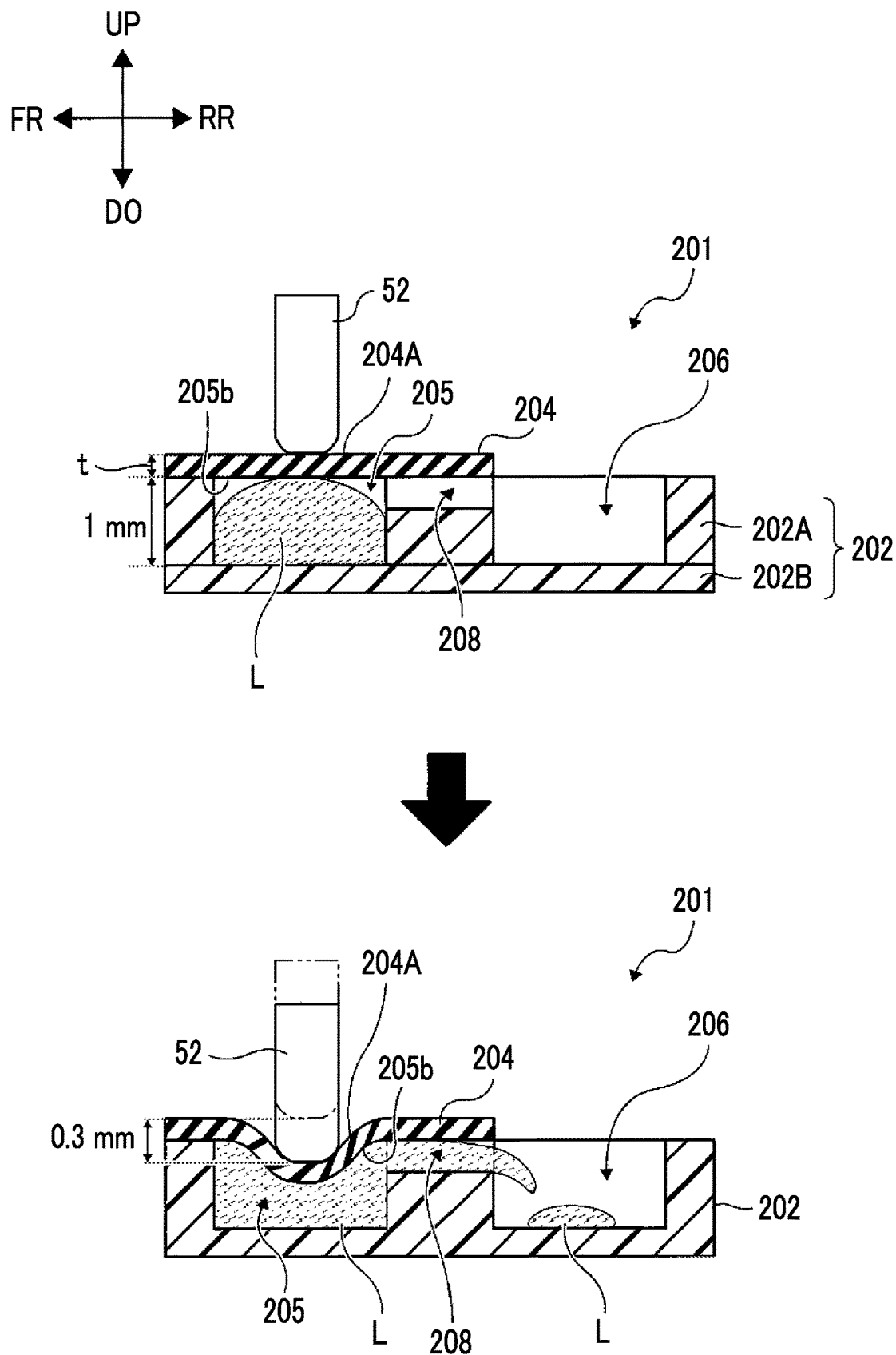
FIG. 16 is a diagram for explaining a measuring method for evaluating liquid feeding properties.

Examples and comparative examples of containers including two accommodation portions and flow paths connecting those to each other were prepared and evaluated. FIG. 15 is a plan view showing a main body portion 202 of the test container of examples and comparative examples. FIG. 16 is a diagram for explaining a measuring method for evaluating liquid feeding properties. The test container 201 of each example includes two accommodation portions 205 and 206, and a flow path 208 connecting the two accommodation portions 205 and 206 at the upper end. The two accommodation portions 205 and 206 have the same shape, and have a length L of 7.5 mm, a width W of 7.5 mm, and a depth d of 1 mm. A width of the flow path 208 is set as 1 mm and a height thereof is set as 0.2 mm (that is, an inner bottom surface of the flow path 208 is connected at a height of 0.8 mm from an inner bottom surface of the accommodation portion 205).

The test container 201 is configured with the main body portion 202 and an upper lid member 204, and the main body portion 202 is configured with a main body portion 202A forming side wall surfaces of the accommodation portions 205 and 206 and a side wall surface and an inner bottom surface of the flow path 208, and a bottom surface member 202B forming the inner bottom surfaces of the accommodation portions 205 and 206.

Polycarbonate (PC) was used as the material of the main body portion 202. Specifically, the main body portion 202A was injection-molded using IUPILON EB-3001R manufactured by Mitsubishi Engineering Plastics Co., Ltd. As the bottom surface member 202B, Technoloy C000 (thickness of 100 μm) manufactured by Sumika Acrylic Sales Co., Ltd. was used. The bottom surface member 202B was roller-bonded to the bottom surface of the main body portion 202A using an adhesive #9969 manufactured by 3M Japan Co., Ltd. to be attached to the main body portion 202. The upper lid member 204 was roller-bonded to the upper surface of the main body portion 202A using a silicone adhesive NSD-50 manufactured by Nipper Co., Ltd. to obtain a test container. Here, as shown in FIG. 16, the upper lid member 204 was attached to the main body portion 202A so that the one accommodation portion and the flow path are covered and the other accommodation portion is opened, for evaluation of the liquid feeding test from the one accommodation portion to the other accommodation portion.

A material and a thickness of the upper lid member 204 were set as follows for each example and comparative example.

Example 1

In the test container of Example 1, a polycarbonate material, Sumika Acrylic Sales Co., Ltd.: Technology (thickness of 100 μm) was used as the upper lid member 204.

Example 2

In the test container of Example 2, a polyolefin-based material, Toray Industries, Inc.: Trefan BO (thickness of 60 μm) was used as the upper lid member 204.

Example 3

In the test container of Example 3, a polyolefin-based material, SunTox Co., Ltd.: SunTox-CP YJ02 (thickness of 30 μm) was used as the upper lid member 204.

Example 4

In the test container of Example 4, a film having a thickness of 90 μm manufactured by adhering three sheets of a polyolefin-based material, SunTox Co., Ltd.: SunTox-CP YJ02 (thickness of 30 μm) to a vacuum laminator was used as the upper lid member 204.

Example 5

In the test container of Example 5, a polyester-based material, Toyobo Co., Ltd.: Cosmoshine A4300 (thickness of 50 μm) was used as the upper lid member 204.

Example 6

In the test container of Example 6, a fluorine-based resin material, Daikin Industries, Ltd.: NEOFLON PFA AF-0100 (thickness of 100 μm) was used as the upper lid member 204.

Example 7

In the test container of Example 7, a fluorine-based resin material, Daikin Industries, Ltd.: NEOFLON ETFE EF-0100 (thickness of 100 μm) was used as the upper lid member 204.

Example 8

In the test container of Example 8, silicone, Tomita Mateqs Co., Ltd.: GFSC6000 (thickness of 100 μm) was used as the upper lid member 204.

Example 9

In the test container of Example 9, silicone, Tomita Mateqs Co., Ltd.: GFSC6000 (thickness of 200 μm) was used as the upper lid member 204.

Example 10

In the test container of Example 10, silicone, Tomita Mateqs Co., Ltd.: GFSC6000 (thickness of 300 μm) was used as the upper lid member 204.

Example 11

In the test container of Example 11, silicone, Tomita Mateqs Co., Ltd.: GFSC6000 (thickness of 1,000 μm) was used as the upper lid member 204.

Example 12

In the test container of Example 12, a polyolefin-based material, UNITIKA Ltd., cast film of Arrowbase SE1013N (thickness of 200 μm) was used as the upper lid member 204.

The cast film was manufactured by the following procedure.

Manufacturing of Cast Film

A resin composition 1 obtained by mixing the following components was poured into a PFA Petri dish manufactured by Tokyo Materials Co., Ltd. so that a dry film thickness was 200 μm, dried at 30° C. for 10 days, and then heated at 100° C. for 10 minutes. Then, the dry film was peeled from the Petri dish to obtain a cast film.

The resin composition 1 in the manufacturing of the cast film was obtained by mixing the following components.

Resin Composition 1

As the resin composition 1, a mixture of the following components was used.

Arrowbase SE1013N (UNITIKA Ltd.): 98.00 parts by mass

Fluorine-based surfactant (sodium=bis(3,3,4,4,5,5,6,6,6-nonafluorohexyl)=2-sulfonite oxysuccinate, manufactured by FUJIFILM Fine Chemicals Co., Ltd., 2% water dilution): 2.00 parts by mass

Example 13

In the test container of Example 13, a polyolefin-based material, UNITIKA Ltd., cast film of Arrowbase SE1013N (thickness of 400 μm) was used as the upper lid member 204. The cast film was manufactured by the following procedure.

Manufacturing of Cast Film

The resin composition 1 obtained in Example 12 was poured into a PFA Petri dish manufactured by Tokyo Materials Co., Ltd. so that a dry film thickness was 400 μm, dried at 30° C. for 10 days, and then heated at 100° C. for 10 minutes. Then, the dry film was peeled from the Petri dish to obtain a cast film.

Example 14

In the test container of Example 14, a polyolefin-based material, Toho Chemical Industry Co., Ltd, case film of Hitech S3121 (thickness of 600 μm) was used as the upper lid member.

The cast film was manufactured by the following procedure.

Manufacturing of Cast Film

A resin composition 2 obtained by mixing the following components was poured into a PFA Petri dish manufactured by Tokyo Materials Co., Ltd. so that a dry film thickness was 600 μm, dried at 30° C. for 10 days, and then heated at 100° C. for 10 minutes. Then, the dry film was peeled from the Petri dish to obtain a cast film.

The resin composition 2 in the manufacturing of the cast film was obtained by mixing the following components.

Resin Composition 2

As the resin composition 2, a mixture of the following components was used.

High Tech S3121 (Toho Chemical Industry Co., Ltd.): 97.53 parts by mass

Fluorine-based surfactant (sodium=bis(3,3,4,4,5,5,6,6, 6-nonafluorohexyl)=2-sulfonite oxysuccinate, manufactured by FUJIFILM Fine Chemicals Co., Ltd., 2% water dilution): 2.47 parts by mass Example 15

In the test container of Example 15, a polyolefin-based material, Toho Chemical Industry Co., Ltd, case film of Hitech S3121 (thickness of 800 μm) was used as the upper lid member.

The cast film was manufactured in the same manner as in Example 14. That is, a cast film having a dry film thickness of 800 μm was manufactured using the resin composition 2.

Example 16

In the test container of Example 16, a polyolefin-based material, UNITIKA Ltd., cast film of Arrowbase DA1010 (thickness of 500 μm) was used as the upper lid member.

The cast film was manufactured by the following procedure.

Manufacturing of Cast Film

A resin composition 3 obtained by mixing the following components was poured into a PFA Petri dish manufactured by Tokyo Materials Co., Ltd. so that a dry film thickness was 500 μm, dried at 30° C. for 10 days, and then heated at 100° C. for 10 minutes. Then, the dry film was peeled from the Petri dish to obtain a cast film.

The resin composition 3 in the manufacturing of the cast film was obtained by mixing the following components.

Resin Composition 3

As the resin composition 3, a mixture of the following components was used.

Arrowbase DA1010 (UNITIKA Ltd.): 97.56 parts by mass

Fluorine-based surfactant (sodium=bis(3,3,4,4,5,5,6,6, 6-nonafluorohexyl)=2-sulfonite oxysuccinate, manufactured by FUJIFILM Fine Chemicals Co., Ltd., 2% water dilution): 2.44 parts by mass Example 17

In the test container of Example 17, a polyolefin-based material, Sumitomo Seika Chemicals Co., Ltd., cast film of SEPOLSION VA-407 (thickness of 1,500 μm) was used as the upper lid member.

The cast film was manufactured by the following procedure.

Manufacturing of Cast Film

A resin composition 4 obtained by mixing the following components was poured into a PFA Petri dish manufactured by Tokyo Materials Co., Ltd. so that a dry film thickness was 1,500 μm, dried at 30° C. for 10 days, and then heated at 100° C. for 10 minutes. Then, the dry film was peeled from the Petri dish to obtain a cast film.

The resin composition 4 in the manufacturing of the cast film was obtained by mixing the following components.

Resin Composition 4

As the resin composition 4, a mixture of the following components was used.

Pure water: 37.71 parts by mass

SEPOLSION VA-407 (Sumitomo Seika Co., Ltd.): 59.70 parts by mass

Fluorine-based surfactant (sodium=bis(3,3,4,4,5,5,6,6, 6-nonafluorohexyl)=2-sulfonite oxysuccinate, manufactured by FUJIFILM Fine Chemicals Co., Ltd., 2% water dilution): 2.99 parts by mass Example 18

In the test container of Example 18, a polyolefin-based material, Sumitomo Seika Chemicals Co., Ltd., cast film of SEPOLSION VA-407 (thickness of 2,000 μm) was used as the upper lid member.

Comparative Example 1

In the test container of Comparative Example 1, silicone, Sumika Acrylic Sales Co., Ltd.: Technoloy C000 (thickness of 100 μm) was used as the upper lid member 204.

Comparative Example 2

In the test container of Comparative Example 2, silicone, Shin-Etsu Chemical Co., Ltd.: KER-4700-UV (thickness of 100 μm) was used as the upper lid member 204. KER-4700-UV was applied to Therapy RX manufactured by Toray Co., Ltd. to have a thickness of 100 μm, and then the curing treatment was performed by irradiating with light of a metal halide lamp (MAL625NAL manufactured by GS Yuasa International Ltd.) having an exposure intensity of 300 mJ/cm$^2$ in a low oxygen atmosphere having an oxygen concentration of 1,000 ppm or less. Finally, the therapy was peeled off to obtain a film having a thickness of 100 μm.

Comparative Example 3

In the test container of Comparative Example 3, a polystyrene-based material, Mitsubishi Chemical Corporation: Santo Clear AP (thickness of 180 μm) was used as the upper lid member 204.

With respect to the upper lid members of the containers of Examples 1 to 11 and Comparative Examples 1 to 3 obtained as described above, the modulus of elasticity and the breaking elongation were measured.

Modulus of Elasticity and Break Elongation

The upper lid member of each example was punched to have a width of 10 mm and a length of 50 mm using a punching cutter. A tensile test at a tensile rate of 50 mm/min was performed using Tensileon RTF-1310 manufactured by A&D Co., Ltd. The modulus of elasticity and breaking elongation were obtained from the obtained stress-strain curve. The cast film and the non-stretched film were tested with a film punched in an arbitrary direction, and an average value measured 5 times was used. The stretched film was tested with samples punched in a machine direction (MD) and a transverse direction (TD), and an average value measured 5 times each for MD and TD was used.

The modulus of elasticity and breaking elongation for the upper lid member in each example are shown in Table 1.

The liquid feeding properties of the containers of Examples 1 to 11 and Comparative Examples 1 to 3 were evaluated by the following method.

Evaluation of Liquid Feeding Properties

After filling the one accommodation portion 205 in the test container with water, the ball plunger 52 as a pressing portion was pushed to the vicinity of the center of the portion 204A forming the upper wall surface 205b of the accommodation portion 205 by 0.3 mm. Accordingly, the liquid fed to the other accommodation portion 206 was recovered and weighed. An average value measured 5 times was evaluated according to the following criteria. Practically, D or higher is required. In addition, practically, C or higher is preferable, B or higher is more preferable, and A is further preferable.

A: 1 mg or more
B: less than 1 mg and 0.75 mg or more
C: less than 0.75 mg and 0.5 mg or more
D: less than 0.5 mg and 0.25 mg or more
E: Less than 0.25 mg, or the film was damaged during each measurement, and the measurement could not be performed.

Table 1 collectively shows a structure, measurement, and evaluation results of the test container of each example.

obtained, compared to Comparative Examples 1 to 3 in which the breaking elongation was less than 100%.

In Examples 3, 4, 6 to 14, 17, the relationships of $0.03 \le t/d \le 1.8$ and $2{,}000 \le \alpha \times t \le 110{,}000$ were satisfied and the liquid feeding properties were higher than those in Examples 1, 2, 5, 15, 16, and 18. These were evaluated as the liquid feeding properties at the level of C or higher.

Among those, in Examples 4 and 7 to 13, the relationships of $0.08 \le t/d \le 1.0$ and $2{,}000 \le \alpha \times t \le 50{,}000$ were satisfied and the liquid feeding properties were higher than those in Examples 3, 5, 6, 14, and 17. These were evaluated as the liquid feeding properties at the level of B or higher.

Among those, in Examples 9, 10, and 12, the relationships of $0.2 \le t/d \le 0.4$ and $4{,}000 \le \alpha \times t \le 20{,}000$ were satisfied and the liquid feeding properties were highest among Examples 1 to 11. These were evaluated as the liquid feeding properties at the level of A.

TABLE 1

| | Test container | | | | | | | |
|---|---|---|---|---|---|---|---|---|
| | Container main body | Upper lid member | | | | | | |
| | | | | Physical properties | | | | |
| | Accommodation portion depth d | Material | | Thickness t | Breaking elongation | Modulus of elasticity | Modulus of elasticity α × thickness t | Thickness t/accommodation portion depth d | Evaluation Liquid feeding properties |
| | [μm] | Type | Product number | [μm] | [%] | α [MPa] | [MPa· μm] | | |
| Example 1 | 1000 | Polycarbonate-based | Technoloy C000 | 100 | 105 | 1568 | 156800 | 0.100 | D |
| Example 2 | 1000 | Polyolefin-based | Trefan BO | 60 | 110 | 2032 | 121920 | 0.060 | D |
| Example 3 | 1000 | Polyolefin-based | SunTox-CP YJ02 | 30 | 600 | 70 | 2100 | 0.030 | C |
| Example 4 | 1000 | Polyolefin-based | SunTox-CP YJ02 | 90 | 511 | 68 | 6120 | 0.090 | B |
| Example 5 | 1000 | Polyester-based | Cosmoshine A4300 | 50 | 133 | 4316 | 215800 | 0.050 | D |
| Example 6 | 1000 | Fluorine-based | NEOFLON AF-0100 | 100 | 467 | 732 | 73200 | 0.100 | C |
| Example 7 | 1000 | Fluorine-based | NEOFLON EF-0100 | 100 | 494 | 480 | 48000 | 0.100 | B |
| Example 8 | 1000 | Silicone | GFSC6000 | 100 | 165 | 22 | 2200 | 0.100 | B |
| Example 9 | 1000 | Silicone | GFSC6000 | 200 | 203 | 20 | 4000 | 0.200 | A |
| Example 10 | 1000 | Silicone | GFSC6000 | 300 | 262 | 17 | 5100 | 0.300 | A |
| Example 11 | 1000 | Silicone | GSSC6000 | 1000 | 114 | 14 | 14000 | 1.000 | B |
| Example 12 | 1000 | Polyolefin-based | Arrowbase SE1013N | 200 | 331 | 100 | 20000 | 0.200 | A |
| Example 13 | 1000 | Polyolefin-based | Arrowbase SE1013N | 400 | 343 | 124 | 49600 | 0.400 | B |
| Example 14 | 1000 | Polyolefin-based | Hitech S3121 | 600 | 322 | 155 | 93000 | 0.600 | C |
| Example 15 | 1000 | Polyolefin-based | Hitech S3121 | 800 | 280 | 150 | 120000 | 0.800 | D |
| Example 16 | 1000 | Polyolefin-based | Arrowbase DA1010 | 500 | 280 | 364 | 182000 | 0.500 | D |
| Example 17 | 1000 | Polyolefin-based | SEPOLSION VA-407 | 1500 | 437 | 65 | 97500 | 1.500 | C |
| Example 18 | 1000 | Polyolefin-based | SEPOLSION VA-407 | 2000 | 403 | 61 | 122000 | 2.000 | D |
| Comparative Example 1 | 1000 | Acryl | Technoloy S000 | 100 | 22 | 1591 | 159057 | 0.100 | E |
| Comparative Example 2 | 1000 | Silicone | KER-4700-UV | 100 | 20 | 302 | 30200 | 0.100 | E |
| Comparative Example 3 | 1000 | Polystyrene | Santo Clear SP | 180 | 15 | 2655 | 477900 | 0.180 | E |

In FIG. 17, the graph was plotted by setting the vertical axis as the upper lid member thickness/accommodation portion depth (t/d) and the horizontal axis as the modulus of elasticity×the thickness of the upper lid member (α×t) for the examples, and a range in which it is expected that the liquid feeding properties A to D are obtained based on the evaluation results of each example is shown. In the drawing, the data points of each example are shown with the example number.

As shown in Table 1, in Examples 1 to 18 in which the breaking elongation of the upper lid member was in a range of 100% to 600%, the liquid feeding properties are at a level of D or higher and excellent liquid feeding properties were

EXPLANATION OF REFERENCES 1, 2, 3, 4, 5, 6, 60: Test container
10, 10B, 10C, 10E, 10F, 10G: Container main body
12, 12B, 12C, 12E, 12F, 12G: Main body portion
14: Upper lid member
14A: Portion
21: First accommodation portion
21a: Inner bottom surface of first accommodation portion
21b: Upper wall surface of first accommodation portion
22: Second accommodation portion
22a: Inner bottom surface of second accommodation portion 22b: upper wall surface of second accommodation portion
22c: Inner side surface of second accommodation portion
23: Third accommodation portion
31: First flow path
31a: Inner bottom surface of first flow path
31b: Upper wall surface of first flow path
32: Second flow path
32a: Inner wall surface of second flow path
32b: Upper wall surface of first flow path
34: Hydrophobic surface
40: Stepped portion
41, 42: Step
50: Pressing machine
52: Plunger
54: Cylinder
60: Test container
62: Main body portion
64: Upper lid member
64A: Portion
65: One accommodation portion
65a: Inner bottom surface of one accommodation portion
65b: Upper wall surface of one accommodation portion
66: Other accommodation portion
66a: Inner bottom surface of other accommodation portion
66b: Upper wall surface of other accommodation portion
68: Flow path
68a: Inner bottom surface of flow path
68b: Upper wall surface of flow path
70: Liquid feeding device
100: nucleic acid extraction test device
101: test container
102: Transportation unit
106: Dispenser
107: Magnetic field generation and movement unit
108: Temperature control unit
110: Container main body
112: Main body portion
114: Upper lid member
120: Magnetism collecting chamber (accommodation portion)
121: Cleaning chamber (first accommodation portion)
122: PCR chamber (second accommodation portion)
122a: Inner bottom surface of PCR chamber
123: Detection chamber (third accommodation portion)
125: Chromatographic carrier accommodation portion
128: Chromatographic carrier
130, 131, 132, 135, 145: flow path
150: specimen solution
151: Cleaning solution
152: PCR solution
153: Development solution
160-163: Syringe
170: Movement mechanism
201: Test container
202: Main body portion
202A: Main body portion
202B: Bottom surface member
204: Upper lid member
204A: Portion
205: One accommodation portion
205b: Upper wall surface of one accommodation portion
206: Other accommodation portion
208: flow path

What is claimed is:

1. A test container comprising:
at least two accommodation portions each accommodating a liquid and internally provided;
a flow path connecting the two accommodation portions to each other at respective upper end positions thereof and internally provided; and
a flexible film deformable inwards of at least one accommodation portion at a portion forming an upper wall surface of the one accommodation portion,
wherein the liquid accommodated in the one accommodation portion is fed to the other accommodation portion via the flow path due to deformation of the flexible film towards the one accommodation portion, and
a breaking elongation of the flexible film is 100% or more and 600% or less.

2. The test container according to claim 1,
wherein, in a case where a thickness of the flexible film is t μm, a modulus of elasticity of the flexible film is β MPa, and a depth of the one accommodation portion is d μm,
relationships of $0.03 \leq t/d \leq 2.5$ and $2{,}000 \leq \beta \times t \leq 250{,}000$ are satisfied.

3. The test container according to claim 2,
wherein relationships of $0.03 \leq t/d \leq 1.8$ and $2{,}000 \leq \beta \times t \leq 110{,}000$ are satisfied.

4. The test container according to claim 2,
wherein relationships of $0.08 \leq t/d \leq 1.0$ and $2{,}000 \leq \beta \times t \leq 50{,}000$ are satisfied.

5. The test container according to claim 2,
wherein relationships of $0.2 \leq t/d \leq 0.4$ and $4.000 \leq \beta \times t \leq 20.000$ are satisfied.

6. The test container according to claim 1,
wherein the breaking elongation is 200% to 500%.

7. The test container according to claim 1, further comprising:
a container main body portion in which a portion forming each of the at least two accommodation portions and the flow path is open; and
an upper lid member including the flexible film,
wherein the at least two accommodation portions and the flow path are internally formed by covering an opening of the container main body portion with the upper lid member.

8. The test container according to claim 7,
wherein the upper lid member has flexibility over an entire area.

9. The test container according to claim 1,
wherein the flexible film consists of any of a silicone resin, a fluororesin, polyolefin, and polycarbonate.

10. The test container according to claim 1, comprising:
a first accommodation portion; a second accommodation portion as the one accommodation portion; a third accommodation portion as the other accommodation portion;
a first flow path connecting the first accommodation portion and the second accommodation portion to each other at respective upper end positions thereof; and
a second flow path connecting the second accommodation portion and the third accommodation portion to each other at respective upper end positions thereof.

11. The test container according to claim 10, comprising:
a liquid return prevention structure which prevents a backflow of the liquid to the first accommodation portion, in a case where the liquid accommodated in the second accommodation portion is fed to the third accommodation portion via the second flow path due to deformation of the flexible film toward the second accommodation portion.

12. The test container according to claim 11, wherein the liquid return prevention structure has a structure in which a height from an inner bottom surface of the second accommodation portion to an inner bottom surface of the first flow path is higher than a height from the inner bottom surface of the second accommodation portion to an inner bottom surface of the second flow path.

13. The test container according to claim 11, wherein the liquid return prevention structure has a structure of the first flow path and the second flow path in which a water contact angle of an inner surface of the first flow path is set to be greater than a water contact angle of an inner surface of the second flow path.

14. The test container according to claim 11, wherein the liquid return prevention structure has a structure of a stepped portion which is provided between the first flow path and the second accommodation portion and which includes two or more steps from an inner bottom surface of the second accommodation portion.

15. The test container according to claim 10, further comprising:
   a chromatographic carrier for performing a nucleic acid test; and
   a carrier accommodation portion accommodating the chromatographic carrier.

16. The test container according to claim 10, wherein the first accommodation portion accommodates a first liquid containing magnetic particles,
   the second accommodation portion accommodates separated magnetic particles separated from the first liquid, and
   the first flow path allows the separated magnetic particles to pass.

* * * * *